US012673986B2

(12) United States Patent
Christophe et al.

(10) Patent No.: US 12,673,986 B2
(45) Date of Patent: Jul. 7, 2026

(54) ANTI-PROTEASE NEXIN-1 CONFORMATIONAL SINGLE DOMAIN ANTIBODIES AND USES THEREOF TO CONTROL BLEEDING

(71) Applicants:INSERM (INSTITUT NATIONAL DE LA SANTÉ ET DE LA RECHERCHE MÉDICALE), Paris (FR); UNIVERSITE DE PARIS, Paris (FR); UNIVERSITÉ PARIS-SA-CLAY, Gif-sur-Yvette (FR); UNIVERSITÉ PARIS XIII PARIS-NORD, Villetaneuse (FR)

(72) Inventors: Olivier Christophe, le Kremlin-Bicêtre (FR); Peter Lenting, le Kremlin-Bicêtre (FR); Cécile Denis, le Kremlin-Bicêtre (FR); Marie-Christine Bouton, Paris Cedex (FR)

(73) Assignees: INSERM (Institut National de la Santé et de la Recherche Médicale), Paris (FR); Université de Paris, Paris (FR); UNIVERSITÉ PARIS-SACLAY, Gif-sur-Yvette (FR); UNIVERSITÉ PARIS XIII PARIS-NORD, Villetaneuse (FR)

( * ) Notice: Subject to any disclaimer, the term of this patent is extended or adjusted under 35 U.S.C. 154(b) by 1088 days.

(21) Appl. No.: 17/620,381

(22) PCT Filed: Jun. 19, 2020

(86) PCT No.: PCT/EP2020/067168
§ 371 (c)(1),
(2) Date: Dec. 17, 2021

(87) PCT Pub. No.: WO2020/254619
PCT Pub. Date: Dec. 24, 2020

(65) Prior Publication Data
US 2022/0259295 A1 Aug. 18, 2022

(30) Foreign Application Priority Data
Jun. 20, 2019 (EP) .................................... 19305797

(51) Int. Cl.
*C07K 16/18* (2006.01)
*A61P 7/04* (2006.01)

(52) U.S. Cl.
CPC ............... *C07K 16/18* (2013.01); *A61P 7/04* (2018.01); *C07K 2317/22* (2013.01); *C07K 2317/33* (2013.01); *C07K 2317/35* (2013.01); *C07K 2317/565* (2013.01); *C07K 2317/567* (2013.01); *C07K 2317/569* (2013.01); *C07K 2317/76* (2013.01)

(58) Field of Classification Search
None
See application file for complete search history.

(56) References Cited

FOREIGN PATENT DOCUMENTS

CA       2744555 A1 *  6/2010  ............. A61K 38/57
WO   2012/110843 A1    8/2012
WO   2016/124568 A1    8/2016
WO   2016/166110 A1   10/2016

OTHER PUBLICATIONS

Yau (Journal of Immunological Methods, vol. 297, p. 213-224, 2005) (Year: 2005).*
Rudikoff et al. (Proc Natl Acad Sci USA 79: 1979-1983, 1982) (Year: 1982).*
De Meyer Thomas et al: "Nanobody-based products as research and diagnostic tools", Trends in Biotechnology, Elsevier Publications, Cambridge, GB, vol. 32, No. 5, Mar. 10, 2014, pp. 263-270.
Muyldermans S ED—Puehler Alf et al: "Single Domain Camel Antibodies: Current Status", Journal of Biotechnology, Elsevier, Amsterdam NL, Jan. 1, 2001, pp. 277-302.
Ivan Peryon et al: "Camelid-derived single-chain antibodies in hemostatis: Mechanistic, diagnostic and therapeutic applications", Research and Practive in Thrombosis and Haemostasis, vol. 4, No., 7, Sep. 9, 2020, pp. 1087-1110.

* cited by examiner

*Primary Examiner* — Laura B Goddard
(74) *Attorney, Agent, or Firm* — WCF IP

(57) ABSTRACT

Protease nexin-1 (PN-1) is a member of the serine protease inhibitor (Serpin)-family, with thrombin as its main target. Current polyclonal and monoclonal antibodies against PN-1 frequently cross-react with Plasminogen activator inhibitor-1 (PAI-1), a structurally and functionally homologous Serpin. Herein the inventors develop inhibitory single-domain antibodies (VHHs) showing specific binding to both human (hPN-1) and murine (mPN-1) PN-1 and which de not cross-react with PAI-1. Importantly, all VHHs could block PN-1 activity in plasma as well as PN-1 released from activated platelets, one of the main sources of PN-1 during hemostasis. Thus, the present invention relates to anti-protease nexin-1 (PN-1) conformational single domain antibodies and uses thereof in particular in the therapeutic field for the treatment of haemorrhagic diseases.

Figure 1:
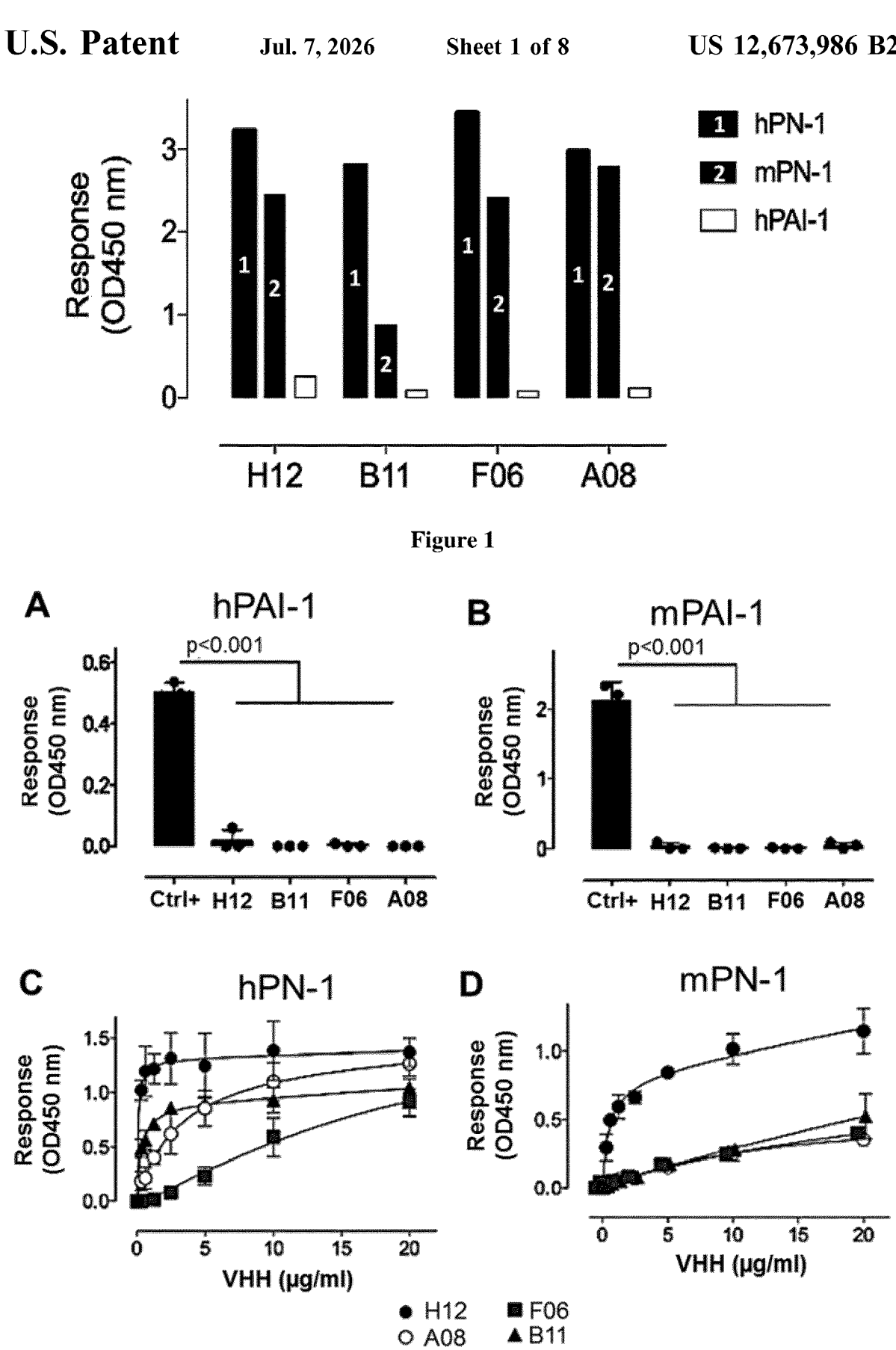

12 Claims, 8 Drawing Sheets
Specification includes a Sequence Listing.

Figure 2A-D

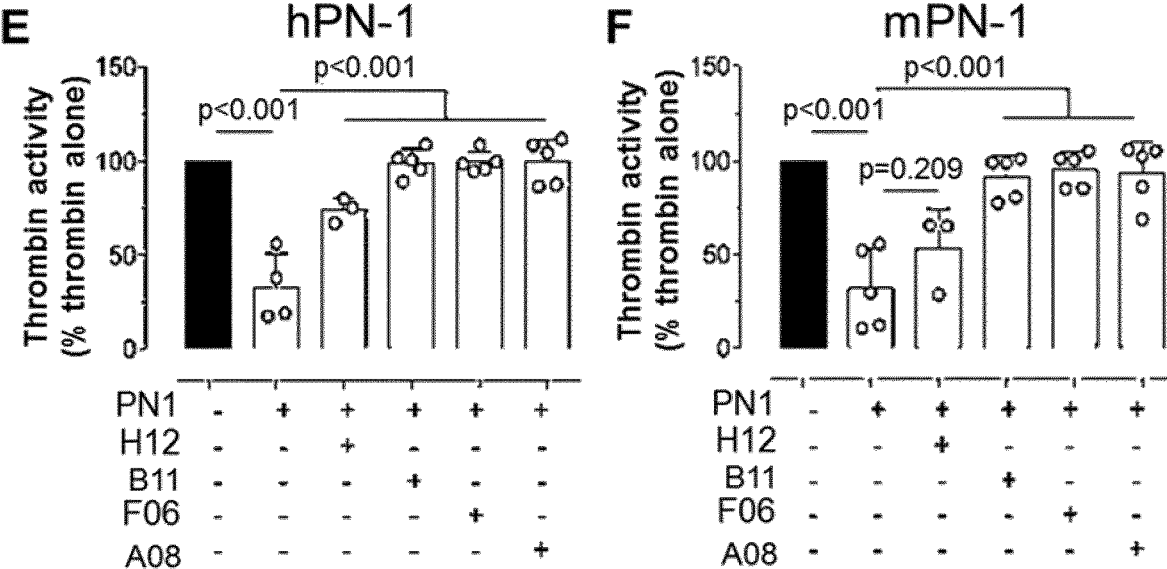
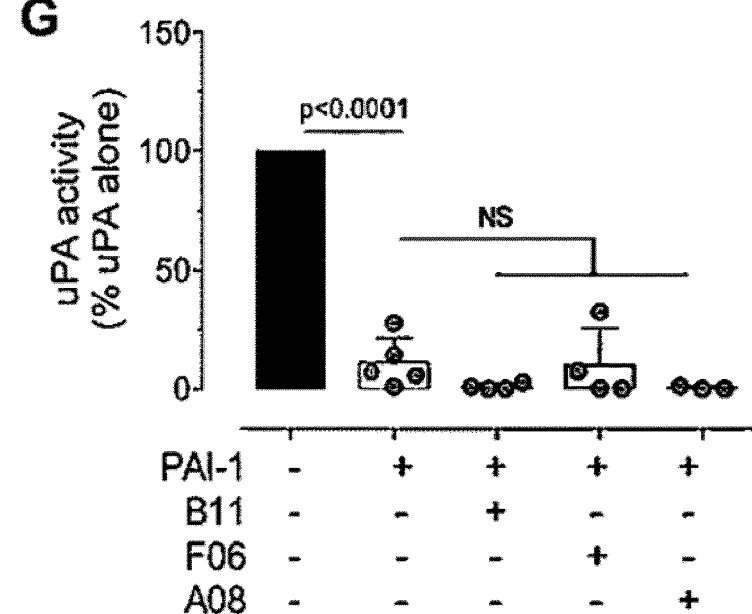
Figure 2E-G

Figure 3A

B
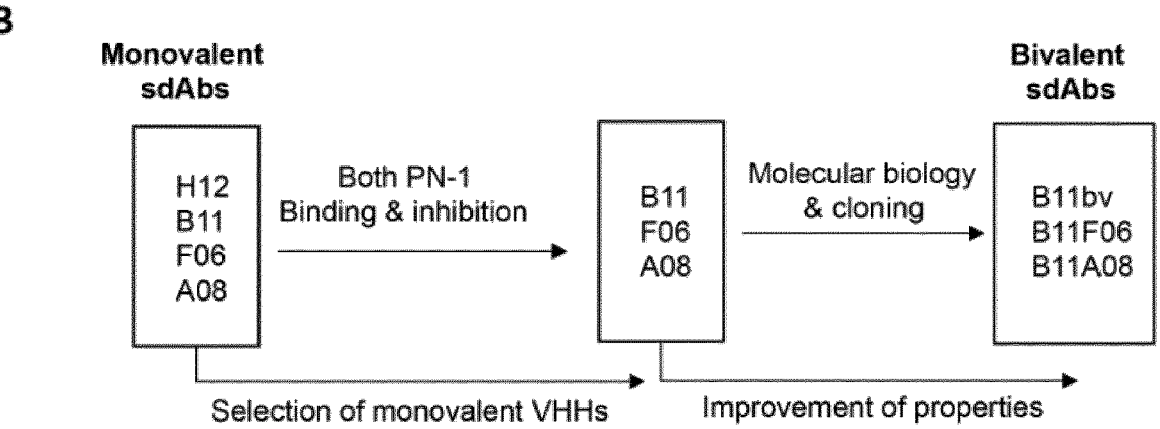
Figure 3B
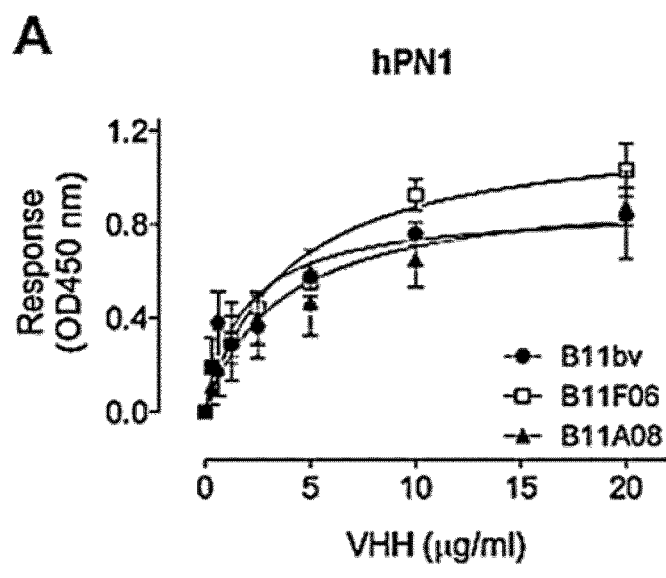
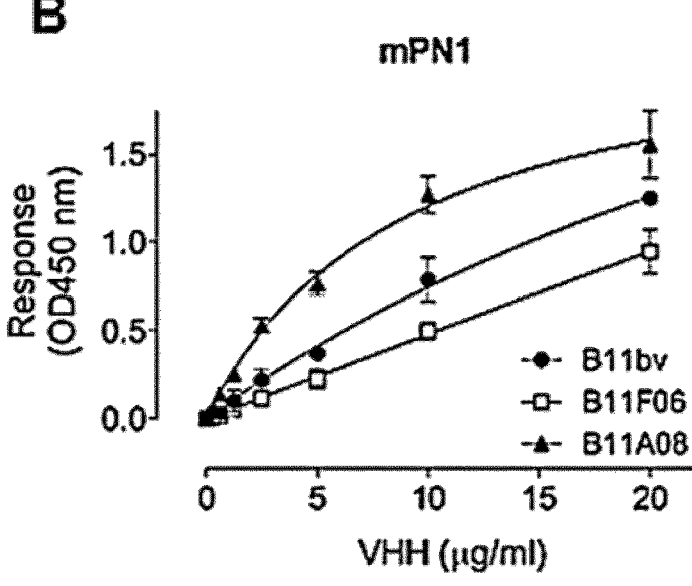
Figure 4A and 4B

Figure 4C

A Modified prothrombin time

B Modified activated partial thromboplastin time

C    *non-activated platelets*

D    *activated platelets*

SEQUENCE LISTING

```
<160> NUMBER OF SEQ ID NOS: 28

<210> SEQ ID NO 1
<211> LENGTH: 7
<212> TYPE: PRT
<213> ORGANISM: Artificial Sequence
<220> FEATURE:
<223> OTHER INFORMATION: Synthetic B11 CDR1

<400> SEQUENCE: 1

Ser Thr Trp Phe Arg Glu Ile
1               5

<210> SEQ ID NO 2
<211> LENGTH: 7
<212> TYPE: PRT
<213> ORGANISM: Artificial Sequence
<220> FEATURE:
```

<223> OTHER INFORMATION: Synthetic B11 CDR2

<400> SEQUENCE: 2

Ser Asp Pro Thr Trp His Ala
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic B11 CDR3

<400> SEQUENCE: 3

Pro Leu Ala Gly Thr Glu Ser Ile His Trp Trp Asp Pro Trp His Glu
1               5                   10                  15

Ser Ser

<210> SEQ ID NO 4
<211> LENGTH: 128
<212> TYPE: PRT
<213> ORGANISM: Artificial Sequence
<220> FEATURE:
<223> OTHER INFORMATION: Synthetic B11

<400> SEQUENCE: 4

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Trp Phe Arg Glu
            20                  25                  30

Ile Met Gly Trp Phe Arg Gln Ala Pro Gly Lys Glu Arg Glu Phe Val
        35                  40                  45

Ser Ala Ile Ser Ser Asp Pro Thr Trp His Ala Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Leu Ala Gly Thr Glu Ser Ile His Trp Trp Asp Pro Trp
            100                 105                 110

His Glu Ser Ser Tyr Trp Gly Gln Gly Thr Gln Val Thr Val Ser Ser
        115                 120                 125

<210> SEQ ID NO 5
<211> LENGTH: 7
<212> TYPE: PRT
<213> ORGANISM: Artificial Sequence
<220> FEATURE:
<223> OTHER INFORMATION: Synthetic F06 CDR1

<400> SEQUENCE: 5

Asp Thr Trp Ser Leu Glu Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic F06 CDR2

<400> SEQUENCE: 6

-continued

```
Ser Glu Asp Gly Trp His Ala
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic F06 CDR3

<400> SEQUENCE: 7

Lys Ile Glu Asn Trp Ile Gln Ala Val Glu Gly Glu Met Ser Asp
1               5                   10                  15

<210> SEQ ID NO 8
<211> LENGTH: 125
<212> TYPE: PRT
<213> ORGANISM: Artificial Sequence
<220> FEATURE:
<223> OTHER INFORMATION: Synthetic F06

<400> SEQUENCE: 8

Glu Val Gln Leu Gln Ala Ser Gly Gly Gly Phe Val Gln Pro Gly Gly
1               5                   10                  15

Ser Leu Arg Leu Ser Cys Ala Ala Ser Gly Asp Thr Trp Ser Leu Glu
            20                  25                  30

Ile Met Gly Trp Phe Arg Gln Ala Pro Gly Lys Glu Arg Glu Phe Val
        35                  40                  45

Ser Ala Ile Ser Ser Glu Asp Gly Trp His Ala Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Lys Ile Glu Asn Trp Ile Gln Ala Val Glu Gly Glu Met Ser
            100                 105                 110

Asp Tyr Trp Gly Gln Gly Thr Gln Val Thr Val Ser Ser
        115                 120                 125

<210> SEQ ID NO 9
<211> LENGTH: 7
<212> TYPE: PRT
<213> ORGANISM: Artificial Sequence
<220> FEATURE:
<223> OTHER INFORMATION: Synthetic A08 CDR1

<400> SEQUENCE: 9

Tyr Tyr Ser Tyr Ser Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic A08 CDR2

<400> SEQUENCE: 10

Phe Tyr Ser Asp Met Ala His
1               5

<210> SEQ ID NO 11
<211> LENGTH: 9
```

-continued

```
<212> TYPE: PRT
<213> ORGANISM: Artificial Sequence
<220> FEATURE:
<223> OTHER INFORMATION: Synthetic A08 CDR3

<400> SEQUENCE: 11

Ala Phe Ser Lys Leu Gly Lys Ile Lys
1               5

<210> SEQ ID NO 12
<211> LENGTH: 119
<212> TYPE: PRT
<213> ORGANISM: Artificial Sequence
<220> FEATURE:
<223> OTHER INFORMATION: Synthetic A08

<400> SEQUENCE: 12

Glu Val Gln Leu Gln Ala Ser Gly Gly Gly Phe Val Gln Pro Gly Gly
1               5                   10                  15

Ser Leu Arg Leu Ser Cys Ala Ala Ser Gly Tyr Tyr Ser Tyr Ser Ser
            20                  25                  30

Thr Met Gly Trp Phe Arg Gln Ala Pro Gly Lys Glu Arg Glu Phe Val
        35                  40                  45

Ser Ala Ile Ser Phe Tyr Ser Asp Met Ala His Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Phe Ser Lys Leu Gly Lys Ile Lys Tyr Trp Gly Gln Gly
            100                 105                 110

Thr Gln Val Thr Val Ser Ser
        115

<210> SEQ ID NO 13
<211> LENGTH: 26
<212> TYPE: PRT
<213> ORGANISM: Artificial Sequence
<220> FEATURE:
<223> OTHER INFORMATION: Synthetic FR1

<400> SEQUENCE: 13

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25

<210> SEQ ID NO 14
<211> LENGTH: 19
<212> TYPE: PRT
<213> ORGANISM: Artificial Sequence
<220> FEATURE:
<223> OTHER INFORMATION: Synthetic FR2

<400> SEQUENCE: 14

Met Gly Trp Phe Arg Gln Ala Pro Gly Lys Glu Arg Glu Phe Val Ser
1               5                   10                  15

Ala Ile Ser

<210> SEQ ID NO 15
<211> LENGTH: 39
<212> TYPE: PRT
```

```
<213> ORGANISM: Artificial Sequence
<220> FEATURE:
<223> OTHER INFORMATION: Synthetic FR3

<400> SEQUENCE: 15

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 16
<211> LENGTH: 12
<212> TYPE: PRT
<213> ORGANISM: Artificial Sequence
<220> FEATURE:
<223> OTHER INFORMATION: Synthetic FR4

<400> SEQUENCE: 16

Tyr Trp Gly Gln Gly Thr Gln Val Thr Val Ser Ser
1               5                   10

<210> SEQ ID NO 17
<211> LENGTH: 259
<212> TYPE: PRT
<213> ORGANISM: Artificial Sequence
<220> FEATURE:
<223> OTHER INFORMATION: Synthetic B11-bv

<400> SEQUENCE: 17

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Trp Phe Arg Glu
            20                  25                  30

Ile Met Gly Trp Phe Arg Gln Ala Pro Gly Lys Glu Arg Glu Phe Val
        35                  40                  45

Ser Ala Ile Ser Ser Asp Pro Thr Trp His Ala Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Leu Ala Gly Thr Glu Ser Ile His Trp Trp Asp Pro Trp
            100                 105                 110

His Glu Ser Ser Tyr Trp Gly Gln Gly Thr Gln Val Thr Val Ser Ser
        115                 120                 125

Ala Ala Ala Glu Val Gln Leu Gln Ala Ser Gly Gly Gly Phe Val Gln
    130                 135                 140

Pro Gly Gly Ser Leu Arg Leu Ser Cys Ala Ala Ser Gly Ser Thr Trp
145                 150                 155                 160

Phe Arg Glu Ile Met Gly Trp Phe Arg Gln Ala Pro Gly Lys Glu Arg
                165                 170                 175

Glu Phe Val Ser Ala Ile Ser Ser Asp Pro Thr Trp His Ala Tyr Tyr
            180                 185                 190

Ala Asp Ser Val Lys Gly Arg Phe Thr Ile Ser Arg Asp Asn Ser Lys
        195                 200                 205

Asn Thr Val Tyr Leu Gln Met Asn Ser Leu Arg Ala Glu Asp Thr Ala
    210                 215                 220
```

```
Thr Tyr Tyr Cys Ala Pro Leu Ala Gly Thr Glu Ser Ile His Trp Trp
225                 230                 235                 240

Asp Pro Trp His Glu Ser Ser Tyr Trp Gly Gln Gly Thr Gln Val Thr
                245                 250                 255

Val Ser Ser

<210> SEQ ID NO 18
<211> LENGTH: 269
<212> TYPE: PRT
<213> ORGANISM: Artificial Sequence
<220> FEATURE:
<223> OTHER INFORMATION: Synthetic B11-F06

<400> SEQUENCE: 18

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Trp Phe Arg Glu
            20                  25                  30

Ile Met Gly Trp Phe Arg Gln Ala Pro Gly Lys Glu Arg Glu Phe Val
            35                  40                  45

Ser Ala Ile Ser Ser Asp Pro Thr Trp His Ala Tyr Tyr Ala Asp Ser
        50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Leu Ala Gly Thr Glu Ser Ile His Trp Trp Asp Pro Trp
            100                 105                 110

His Glu Ser Ser Tyr Trp Gly Gln Gly Thr Gln Val Thr Val Ser Ser
        115                 120                 125

Gly Gly Gly Ser Gly Gly Gly Ser Gly Gly Gly Ser Gly Gly Gly Ser
    130                 135                 140

Glu Val Gln Leu Gln Ala Ser Gly Gly Gly Phe Val Gln Pro Gly Gly
145                 150                 155                 160

Ser Leu Arg Leu Ser Cys Ala Ala Ser Gly Asp Thr Trp Ser Leu Glu
                165                 170                 175

Ile Met Gly Trp Phe Arg Gln Ala Pro Gly Lys Glu Arg Glu Phe Val
            180                 185                 190

Ser Ala Ile Ser Ser Glu Asp Gly Trp His Ala Tyr Tyr Ala Asp Ser
        195                 200                 205

Val Lys Gly Arg Phe Thr Ile Ser Arg Asp Asn Ser Lys Asn Thr Val
    210                 215                 220

Tyr Leu Gln Met Asn Ser Leu Arg Ala Glu Asp Thr Ala Thr Tyr Tyr
225                 230                 235                 240

Cys Ala Lys Ile Glu Asn Trp Ile Gln Ala Val Glu Gly Glu Met Ser
            245                 250                 255

Asp Tyr Trp Gly Gln Gly Thr Gln Val Thr Val Ser Ser
            260                 265

<210> SEQ ID NO 19
<211> LENGTH: 263
<212> TYPE: PRT
<213> ORGANISM: Artificial Sequence
<220> FEATURE:
<223> OTHER INFORMATION: Synthetic B11-A08

<400> SEQUENCE: 19
```

-continued

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Trp Phe Arg Glu
            20                  25                  30

Ile Met Gly Trp Phe Arg Gln Ala Pro Gly Lys Glu Arg Glu Phe Val
            35                  40                  45

Ser Ala Ile Ser Ser Asp Pro Thr Trp His Ala Tyr Tyr Ala Asp Ser
        50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Leu Ala Gly Thr Glu Ser Ile His Trp Trp Asp Pro Trp
            100                 105                 110

His Glu Ser Ser Tyr Trp Gly Gln Gly Thr Gln Val Thr Val Ser Ser
            115                 120                 125

Gly Gly Gly Ser Gly Gly Gly Ser Gly Gly Gly Ser Gly Gly Gly Ser
        130                 135                 140

Glu Val Gln Leu Gln Ala Ser Gly Gly Gly Phe Val Gln Pro Gly Gly
145                 150                 155                 160

Ser Leu Arg Leu Ser Cys Ala Ala Ser Gly Tyr Tyr Ser Tyr Ser Ser
            165                 170                 175

Thr Met Gly Trp Phe Arg Gln Ala Pro Gly Lys Glu Arg Glu Phe Val
            180                 185                 190

Ser Ala Ile Ser Phe Tyr Ser Asp Met Ala His Tyr Tyr Ala Asp Ser
            195                 200                 205

Val Lys Gly Arg Phe Thr Ile Ser Arg Asp Asn Ser Lys Asn Thr Val
        210                 215                 220

Tyr Leu Gln Met Asn Ser Leu Arg Ala Glu Asp Thr Ala Thr Tyr Tyr
225                 230                 235                 240

Cys Ala Ala Phe Ser Lys Leu Gly Lys Ile Lys Tyr Trp Gly Gln Gly
                245                 250                 255

Thr Gln Val Thr Val Ser Ser
            260
```

```
<210> SEQ ID NO 20
<211> LENGTH: 7
<212> TYPE: PRT
<213> ORGANISM: Artificial Sequence
<220> FEATURE:
<223> OTHER INFORMATION: Synthetic peptide sequence with variable
      residues
<220> FEATURE:
<221> NAME/KEY: MISC_FEATURE
<222> LOCATION: (1)..(1)
<223> OTHER INFORMATION: X is S or D
<220> FEATURE:
<221> NAME/KEY: MISC_FEATURE
<222> LOCATION: (4)..(4)
<223> OTHER INFORMATION: X is F or R
<220> FEATURE:
<221> NAME/KEY: MISC_FEATURE
<222> LOCATION: (5)..(5)
<223> OTHER INFORMATION: X is R or L

<400> SEQUENCE: 20

Xaa Thr Trp Xaa Xaa Phe Ile
1               5
```

```
<210> SEQ ID NO 21
<211> LENGTH: 7
<212> TYPE: PRT
<213> ORGANISM: Artificial Sequence
<220> FEATURE:
<223> OTHER INFORMATION: Synthetic peptide sequence with variable
      residues
<220> FEATURE:
<221> NAME/KEY: MISC_FEATURE
<222> LOCATION: (2)..(2)
<223> OTHER INFORMATION: X is D or E
<220> FEATURE:
<221> NAME/KEY: MISC_FEATURE
<222> LOCATION: (3)..(3)
<223> OTHER INFORMATION: X is Por D
<220> FEATURE:
<221> NAME/KEY: MISC_FEATURE
<222> LOCATION: (4)..(4)
<223> OTHER INFORMATION: X isT or G

<400> SEQUENCE: 21

Ser Xaa Xaa Xaa Trp His Ala
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic linker

<400> SEQUENCE: 22

Gly Gly Gly Gly Ser Gly Gly Gly Ser Gly Gly Gly Gly Ser
1               5                   10

<210> SEQ ID NO 23
<211> LENGTH: 20
<212> TYPE: PRT
<213> ORGANISM: Artificial Sequence
<220> FEATURE:
<223> OTHER INFORMATION: Synthetic linker

<400> SEQUENCE: 23

Gly Gly Gly Gly Ser Gly Gly Gly Gly Ser Gly Gly Gly Gly Ser Gly
1               5                   10                  15

Gly Gly Gly Ser
            20

<210> SEQ ID NO 24
<211> LENGTH: 5
<212> TYPE: PRT
<213> ORGANISM: Artificial Sequence
<220> FEATURE:
<223> OTHER INFORMATION: Synthetic linker

<400> SEQUENCE: 24

Gly Gly Gly Gly Ser
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic linker

<400> SEQUENCE: 25

Gly Gly Gly Ser
1
```

```
<210> SEQ ID NO 26
<211> LENGTH: 15
<212> TYPE: PRT
<213> ORGANISM: Artificial Sequence
<220> FEATURE:
<223> OTHER INFORMATION: Synthetic linker

<400> SEQUENCE: 26

Gly Gly Gly Ser Ser Gly Gly Gly Ser Ser Gly Gly Gly Ser Ser
1               5                   10                  15

<210> SEQ ID NO 27
<211> LENGTH: 6
<212> TYPE: PRT
<213> ORGANISM: Artificial Sequence
<220> FEATURE:
<223> OTHER INFORMATION: Synthetic histidine tag

<400> SEQUENCE: 27

His His His His His His
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic linker

<400> SEQUENCE: 28

Gly Gly Gly Ser Gly Gly Gly Ser Gly Gly Gly Ser
1               5                   10
```

ANTI-PROTEASE NEXIN-1 CONFORMATIONAL SINGLE DOMAIN ANTIBODIES AND USES THEREOF TO CONTROL BLEEDING

SEQUENCE LISTING

This application includes as the Sequence Listing the complete contents of the accompanying text file "substitute_sequence_listing", created Jun. 20, 2025, containing 16,084 bytes, hereby incorporated by reference.

FIELD OF THE INVENTION

The present invention relates to anti-protease nexin-1 (PN-1) conformational single domain antibodies and uses thereof in particular in the therapeutic field.

BACKGROUND OF THE INVENTION

Current treatments to control bleeding episodes in patients with haemophilia and more generally in patients with constitutive haemorrhagic diseases display many drawbacks. Treatment of these patients with an inhibitor is limited to FVIII- or IX-bypassing agents, such as recombinant FVIIa or plasma-derived activated prothrombin complex. However, these products are expensive and a substantial number of patients do not respond to these agents. Thus, due to the limitations of current treatments which rely mostly on intravenous infusion of recombinant or plasma-derived FVIII or FIX, new strategies have emerged, aiming to target natural anticoagulant proteins.

The inventors previously demonstrated that platelet PN-1 is a negative regulator of both thrombin activity and generation and that PN-1 deficiency facilitates coagulation in vivo (Boulaftali et al. 2010). They showed that targeting PN-1 could thwart FVIII or IX deficiency and demonstrated that blocking PN-1 have a role in haemorrhagic disease treatment.

Herein, the inventors develop inhibitory single-domain antibodies (VHH or nanobodies) targeting platelet protease nexin-1 (PN-1), a natural and potent thrombin inhibitor. The inventors emphasize the difficulties in raising specific antibodies to PN-1. The majority of commercial antibodies to PN-1 that we tested also proved non-specific. The nanobodies of the invention appear to be the first specific biological tools able to block the anti-thrombin activity of both murine and human PN-1. Thus, they are good candidates to block PN-1 in platelets to restore the hemostatic balance in hemophilia patients.

SUMMARY OF THE INVENTION

The protease nexin-1 (PN-1), also known as SERPINE2, is a member of serine protease inhibitors, termed serpins that are key regulators in many biologic events. PN-1 is a serpin that is barely detectable in plasma but found in many organs and produced by most cell types, including monocytes, platelets, and vascular cells. PN-1 is a 45- to 50-kDa glycoprotein that is encoded by the SERPINE2 gene on human chromosome 2q33-q35. PN-1 is a 378 amino acid residue single-chain containing 3 cysteine residues that do not form disulfide bonds within the protein core of the molecule (Bouton et al., 2012 and Mc Grogan et al 1988 Boulaftali et al., 2010). The inventors previously demonstrated that targeting PN-1 improves thrombin generation in mild and moderate hemophilia patient. These findings established a requirement for PN-1 inhibition as a specific anti-coagulant in platelets and demonstrated that blocking PN-1 have a role in haemorrhagic disease treatment.

In the present application, the inventors describe the successful selection and the characterization of anti-protease nexin-1 (PN-1) conformational single domain antibodies. Sequences of said antibodies are depicted in Table 1. Phage display experiments were performed using a llama-derived or a synthetic nanobodies library in order to screen for VHH recognizing both human and murine PN-1. Using a llama-derived library, a total of 7 rounds of panning and 940 tested VHH, resulted in 52 candidates recognizing PN-1. However, careful characterization revealed that all these VHH also recognized plasminogen activator inhibitor-1 (PAI-1). This lack of specificity prompted us to screen a synthetic library, resulting in 7 positive nanobodies binding efficiently to both human and murine PN-1 and without cross-reactivity with others serpins. Four proved able to inhibit the anti-thrombin activity of human and murine PN-1. In particular the inventors isolated 3 different specific anti-PN-1 clones binding to three distinct epitopes. Interesting, all 3 sdAbs was found specific to PN-1 without cross-reactivity with others serpins or plasminogen activator inhibitor-1 (PAI-1). Accordingly, these antibodies appear to be the first specific biological tools to block the anti-thrombin and susceptible to restore the hemostatic balance in haemophilia patients.

Thus, the present invention relates to anti-protease nexin-1 (PN-1) single domain antibodies and uses thereof in particular in the therapeutic field. In particular, the present invention is defined by the claims.

DETAILED DESCRIPTION OF THE INVENTION

The inventors have developed single domain antibodies (sdAb) comprising three specific CDRs that allow a selective binding to protease nexin-1 (PN-1). These sdAb constitutes a performing tool as therapeutic agent.

Definition

As used herein, the term "protease nexin-1" or "PN-1" has its general meaning in the art and refers to the protease nexin-1 also known as SERPINE2. PN-1 has its general meaning in the art and refers to a member of serine protease inhibitors, termed serpins that are key regulators in many biologic events. PN-1 is a serpin that is barely detectable in plasma but found in many organs and produced by most cell types, including monocytes, platelets, and vascular cells. PN-1 is a 45- to 50-kDa glycoprotein that is encoded by the SERPINE2 gene on human chromosome 2q33-q35. PN-1 is a 378 amino acid residue single-chain containing 3 cysteine residues that do not form disulfide bonds within the protein core of the molecule (Bouton et al., 2012 and Mc Grogan et al 1988 Boulaftali et al., 2010).

As used herein the term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents to detect antigens that are otherwise cryptic using classical immunological techniques, and as possible therapeutic agents. Thus yet another consequence of small size is that a nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in nanobodies being extremely thermostable, stable to extreme pH and to proteolytic digestion, and poorly antigenic. Another consequence is that nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system amino acid numbering see the website-located at imgt.cines.fr).

As used herein, the term "amino acid sequence" has its general meaning and is a sequence of amino acids that confers to a protein its primary structure. According to the invention, the amino acid sequence may be modified with one, two or three conservative amino acid substitutions, without appreciable loss of interactive binding capacity. By "conservative amino acid substitution", it is meant that an amino acid can be replaced with another amino acid having a similar side chain. Families of amino acid having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence. Amino acid sequence identity is typically determined using a suitable sequence alignment algorithm and default parameters, such as BLAST P (Karlin and Altschul, 1990).

According to the meaning of the present invention, the "identity" is calculated by comparing two aligned sequences in a comparison window. The sequence alignment allows determining the number of positions (nucleotides or amino acids) in common for the two sequences in the comparison window. The number of positions in common is therefore divided by the total number of positions in the comparison window and multiplied by 100 to obtain the identity percentage. The determination of the identity percentage of sequence can be made manually or thanks to well-known computer programs.

As used herein, the terms "purified" and "isolated" relate to the sdAb of the invention and mean that the sdAb is present in the substantial absence of other biologic macromolecules of the same type. The term "purified" as used here means preferably that at least 75% in weight, more preferably at least 85% in weight, even more preferably at least 95% in weight, and the more preferably at least 98% in weight of antibody, compared to the total weight of macromolecules present.

As used herein, the term "nucleic acid molecule" has its general meaning in the art and refers to a DNA or RNA molecule.

Single Domain Antibodies and Polypeptide

The sequences of interest in the present application are indicated in the following Table 1:

| Name | SEQ ID NO: | SEQUENCE |
|---|---|---|
| B11 CDR1 | 1 | STWFREI |
| B11 CDR2 | 2 | SDPTWHA |
| B11 CDR3 | 3 | PLAGTESIFIWWDPWHESS |
| B11 | 4 | EVQLQASGGGFVQPGGSLRLSCAASGSTWFREIMGWFRQAPG KEREFVSAISSDPTWHAYYADSVKGRFTISRDNSKNTVYLQMN SLRAEDTATYYCAPLAGTESIHWWDPWEIESSYWGQGTQVTVS S |
| F06 CDR1 | 5 | DTWSLEI |
| F06 CDR2 | 6 | SEDGWHA |

-continued

| Name | SEQ ID NO: | SEQUENCE |
|------|-----------|----------|
| F06 CDR3 | 7 | KIENWIQAVEGEMSD |
| F06 | 8 | EVQLQASGGGFVQPGGSLRLSCAASGDTWSLEIMGWFRQAPG<br>KEREFVSAISSEDGWHAYYADSVKGRFTISRDNSKNTVYLQMN<br>SLRAEDTATYYCAKIENWIQAVEGEMSDYWGQGTQVTVSS |
| A08 CDR1 | 9 | YYSYSST |
| A08 CDR2 | 10 | FYSDMAH |
| A08 CDR3 | 11 | AFSKLGKIK |
| A08 | 12 | EVQLQASGGGFVQPGGSLRLSCAASGYYSYSSTMGWFRQAPG<br>KEREFVSAISFYSDMAHYYADSVKGRFTISRDNSKNTVYLQMN<br>SLRAEDTATYYCAAFSKLGKIKYWGQGTQVTVSS |
| FR1 | 13 | EVQLQASGGGFVQPGGSLRLSCAASG |
| FR2 | 14 | MGWFRQAPGKEREFVSAIS |
| FR3 | 15 | YYADSVKGRFTISRDNSKNTVYLQMNSLRAEDTATYYCA |
| FR4 | 16 | YVVGQGTQVTVSS |
| B11-Bv | 17 | EVQLQASGGGFVQPGGSLRLSCAASGSTWFREIMGWFRQAPG<br>KEREFVSAISSDPTWHAYYADSVKGRFTISRDNSKNTVYLQMN<br>SLRAEDTATYYCAPLAGTESIHWWDPWHESSYWGQGTQVTVS<br>S AAA<br>EVQLQASGGGFVQPGGSLRLSCAASGSTWFREIMGWFRQAPG<br>KEREFVSAISSDPTWHAYYADSVKGRFTISRDNSKNTVYLQMN<br>SLRAEDTATYYCAPLAGTESIHWWDPWHESSYWGQGTQVTVS<br>S |
| B11-F06 | 18 | EVQLQASGGGFVQPGGSLRLSCAASGSTWFREIMGWFRQAPG<br>KEREFVSAISSDPTWHAYYADSVKGRFTISRDNSKNTVYLQMN<br>SLRAEDTATYYCAPLAGTESIHAVWDPWEIESSYWGQGTQVTVS<br>S GGGSGGGSGGGSGGGS<br>EVQLQASGGGFVQPGGSLRLSCAASGDTWSLEIMGWFRQAPG<br>KEREFVSAISSEDGWHAYYADSVKGRFTISRDNSKNTVYLQMN<br>SLRAEDTATYYCAKIENWIQAVEGEMSDWGQGTQVTVSS |
| B11-A08 | 19 | EVQLQASGGGFVQPGGSLRLSCAASGSTWFREIMGWFRQAPG<br>KEREFVSAISSDPTWHAYYADSVKGRFTISRDNSKNTVYLQMN<br>SLRAEDTATYYCAPLAGTESIHWWDPWHESSYWGQGTQVTVS<br>S GGGSGGGSGGGSGGGS<br>EVQLQASGGGFVQPGGSLRLSCAASGYYSYSSTMGWFRQAPG<br>KEREFVSAISFYSDMAHYYADSVKGRFTISRDNSKNTVYLQMN<br>SLRAEDTATYYCAAFSKLGKIKYWGQGTQVTVSS |

A first object of the present invention concerns an isolated single domain antibody (sdAb) comprising an amino acid sequence of formula (I) consisting in three complementary determining regions (CDR1 to CDR3) and four framework regions (FR1 to FR4):

FR1-CDR1-FR2-CDR2-FR3-CDR3-FR4 (I); wherein
CDR1 has the following sequence: $X_1$-T-W—$X_4$-$X_5$-E-I (SEQ ID NO: 20), wherein $X_1$ is S or D, $X_4$ is F or R, $X_5$ is R or L; and
CDR2 has the following sequence: S-X2-X3-X4-W-H-A (SEQ ID NO: 21), wherein X2 is D or E, X3 is P or D, X4 is T or G; and
CDR3 has a sequence set forth as SEQ ID NO:3 or SEQ ID NO:7.

In some embodiments the isolated single domain antibody according to the invention comprises a CDR1 having a sequence set forth as SEQ ID NO: 1, a CDR2 having a sequence set forth as SEQ ID NO:2 and a CDR3 having a sequence set forth as SEQ ID NO:3. ("B11 derivative")

In some embodiments the isolated single domain antibody according to the invention comprises a CDR1 having a sequence set forth as SEQ ID NO:5, a CDR2 having a sequence set forth as SEQ ID NO:6 and a CDR3 having a sequence set forth as SEQ ID NO:7. ("F06 derivative")

Another object of the present invention concerns an isolated single domain antibody comprising an amino acid sequence of formula (I) consisting in three complementary determining regions (CDR1 to CDR3) and four framework regions (FR1 to FR4):

FR1-CDR1-FR2-CDR2-FR3-CDR3-FR4 (I); wherein
CDR1 has a sequence set forth as SEQ ID NO:9; and
CDR2 has a sequence set forth as SEQ ID NO:10; and
CDR3 has a sequence set forth as SEQ ID NO:11. ("A08 derivative")

In another word, the present invention concerns an isolated single domain antibody (sdAb) comprising an amino acid sequence of formula (I) consisting in three complementary determining regions (CDR1 to CDR3) and four framework regions (FR1 to FR4):

FR1-CDR1-FR2-CDR2-FR3-CDR3-FR4 (I); wherein
CDR1 has a sequence selected from the group consisting of SEQ ID NO:1; SEQ ID NO:5 and SEQ ID NO:9; and

CDR2 has a sequence selected from the group consisting of SEQ ID NO:2; SEQ ID NO:6 and SEQ ID NO:10; and CDR3 has a sequence selected from the group consisting of SEQ ID NO:3; SEQ ID NO:7 and SEQ ID NO:11.

In some embodiments, FR1 has at least 70% identity with the amino acid sequence SEQ ID NO:13; FR2 has at least 70% identity with the amino acid sequence SEQ ID NO:14; FR3 has at least 70% identity with the amino acid sequence SEQ ID NO:15 and FR4 has at least 70% identity with the amino acid sequence SEQ ID NO:16.

In some embodiments, the isolated single domain antibody according to the invention has at least 70% of identity with sequence set forth as SEQ ID NO:4 ("B11 derivative").

In some embodiments, the isolated single domain antibody according to the invention has at least 70% of identity with sequence set forth as SEQ ID NO:4 and comprises the sequences CDR1, CDR2, CDR3 set forth as SEQ ID NO:1, SEQ ID NO:2 and SEQ ID NO:3.

In some embodiments, the isolated single domain antibody according to the invention comprises the sequence set forth as SEQ ID NO:4 ("B11").

In some embodiments, the isolated single domain antibody according to the invention has the sequence set forth as SEQ ID NO:4.

In some embodiments, the isolated single domain antibody according to the invention has at least 70% of identity with sequence set forth as SEQ ID NO:8 ("F06 derivative").

In some embodiments, the isolated single domain antibody according to the invention has at least 70% of identity with sequence set forth as SEQ ID NO:8 and comprises the sequences CDR1, CDR2, CDR3 set forth as SEQ ID NO:5, SEQ ID NO:6 and SEQ ID NO:7.

In some embodiments, the isolated single domain antibody according to the invention comprises the sequence set forth as SEQ ID NO:8 ("F06").

In some embodiments, the isolated single domain antibody according to the invention has the sequence set forth as SEQ ID NO:8.

In some embodiments, the isolated single domain antibody according to the invention has at least 70% of identity with sequence set forth as SEQ ID NO:12.

In some embodiments, the isolated single domain antibody according to the invention has at least 70% of identity with sequence set forth as SEQ ID NO:12 ("A08 derivative") and comprises the sequences CDR1, CDR2, CDR3 set forth as SEQ ID NO:9, SEQ ID NO:10 and SEQ ID NO:11 ("F06 derivative").

In some embodiments, the isolated single domain antibody according to the invention comprises the sequence set forth as SEQ ID NO:12 ("A08").

In some embodiments, the isolated single domain antibody according to the invention has the sequence set forth as SEQ ID NO:12.

In some embodiments, the isolated single domain antibody is a "humanized" single domain antibody.

As used herein the term "humanized" refers to a single domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favourable properties of single domain antibodies of the invention. The one skilled in the art is able to determine and select suitable humanizing substitutions or suitable combinations of humanizing substitutions.

A further aspect of the invention refers to a cross-competing single domain antibody which cross-competes for binding PN-1 with the single domain antibody of the invention.

In some embodiment, the cross-competing single domain antibody of the present invention cross-competes for binding PN-1 with the single domain antibody comprising an amino acid sequence of formula (I) consisting in three complementary determining regions (CDR1 to CDR3) and four framework regions (FR1 to FR4):

FR1-CDR1-FR2-CDR2-FR3-CDR3-FR4 (I); wherein

CDR1 has the following sequence: $X_1$-T-W—$X_4$-$X_5$-E-I (SEQ ID NO: 20), wherein $X_1$ is S or D, $X_4$ is F or R, $X_5$ is R or L; and CDR2 has the following sequence: S-X2-X3-X4-W-H-A (SEQ ID NO: 21), wherein X2 is D or E, X3 is P or D, X4 is T or G; and CDR3 has a sequence set forth as SEQ ID NO:3 or SEQ ID NO:7.

In some embodiment, the cross-competing single domain antibody of the present invention cross-competes for binding PN-1 with the single domain antibody comprising a CDR1 having a sequence set forth as SEQ ID NO:1, a CDR2 having a sequence set forth as SEQ ID NO:2 and a CDR3 having a sequence set forth as SEQ ID NO:3.

In some embodiment, the cross-competing single domain antibody of the present invention cross-competes for binding PN-1 with the single domain antibody comprising a CDR1 having a sequence set forth as SEQ ID NO:5, a CDR2 having a sequence set forth as SEQ ID NO:6 and a CDR3 having a sequence set forth as SEQ ID NO:7.

In some embodiment, the cross-competing single domain antibody of the present invention cross-competes for binding PN-1 with the single domain antibody comprising a CDR1 having a sequence set forth as SEQ ID NO:9, a CDR2 having a sequence set forth as SEQ ID NO:10 and a CDR3 having a sequence set forth as SEQ ID NO:11.

In some embodiment, the cross-competing single domain antibody of the present invention cross-competes for binding PN-1 with the single domain antibody comprising an amino acid selected from the group consisting of sequence SEQ ID NO:4, SEQ ID NO: 8 and SEQ ID NO:12.

As used herein, the term "cross-competes" refers to single domain antibodies which share the ability to bind to a specific region of an antigen. In the present disclosure the single domain antibody that "cross-competes" has the ability to interfere with the binding of another single domain antibody for the antigen in a standard competitive binding assay. Such a single domain antibody may, according to non-limiting theory, bind to the same or a related or nearby (e.g., a structurally similar or spatially proximal) epitope as the single domain antibody with which it competes. Cross-competition is present if single domain antibody A reduces binding of single domain antibody B at least by 60%, specifically at least by 70% and more specifically at least by 80% and vice versa in comparison to the positive control which lacks one of said single domain antibodies. As the skilled artisan appreciates competition may be assessed in different assay set-ups. One suitable assay involves the use of the Biacore technology (e.g., by using the BIAcore 3000 instrument (Biacore, Uppsala, Sweden)), which can measure the extent of interactions using surface plasmon resonance technology. Another assay for measuring cross-competition uses an ELISA-based approach. Furthermore, a high throughput process for "binning" antibodies based upon their cross-competition is described in International Patent Application No. WO2003/48731.

According to the present invention, the cross-competing antibody as above described retain the activity of the single antibody which comprises a CDR1 having a sequence set forth as SEQ ID NO:1, a CDR2 having a sequence set forth as SEQ ID NO:2 and a CDR3 having a sequence set forth as SEQ ID NO:3.

According to the present invention, the cross-competing antibody as above described retain the activity of the single antibody which comprises a CDR1 having a sequence set forth as SEQ ID NO:5, a CDR2 having a sequence set forth as SEQ ID NO:6 and a CDR3 having a sequence set forth as SEQ ID NO:7

According to the present invention, the cross-competing antibody as above described retain the activity of the single antibody which comprises a CDR1 having a sequence set forth as SEQ ID NO:9, a CDR2 having a sequence set forth as SEQ ID NO:10 and a CDR3 having a sequence set forth as SEQ ID NO:11.

According to the present invention, the cross-competing antibody as above described retain the activity of the single antibody which comprises an amino acid selected from the group consisting of sequence SEQ ID NO:4, SEQ ID NO: 8 and SEQ ID NO:12

A further aspect of the invention refers to a polypeptide comprising at least one single domain antibody of the invention.

Typically, the polypeptide of the invention comprises a single domain antibody of the invention, which is fused at its N terminal end, at its C terminal end, or both at its N terminal end and at its C terminal end to at least one further amino acid sequence, i.e. so as to provide a fusion protein. According to the invention the polypeptides that comprise a sole single domain antibody are referred to herein as "monovalent" polypeptides. Polypeptides that comprise or essentially consist of two or more single domain antibodies according to the invention are referred to herein as "multivalent" polypeptides.

In some embodiments, the polypeptide comprises at least one single domain antibody of the invention and at least one other binding unit (i.e. directed against another epitope, antigen, target, protein or polypeptide), which is typically also a single domain antibody. Such a polypeptide is referred to herein as "multispecific" polypeptide; in opposition to a polypeptide comprising the same single domain antibodies ("monospecific" polypeptide). Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed against, or may be directed against a different protein, polypeptide, antigen, antigenic determinant or epitope) from the single domain antibody of the invention.

A "bispecific" polypeptide of the invention is a polypeptide that comprises at least one single domain antibody directed against a first antigen (i.e. protease nexin-1, PN-1) and at least one further binding site directed against a second antigen (i.e. different from PN-1), whereas a "trispecific" polypeptide of the invention is a polypeptide that comprises at least one single domain antibody directed against a first antigen (i.e. PN-1), at least one further binding site directed against a second antigen (i.e. different from PN-1) and at least one further binding site directed against a third antigen (i.e. different from both i.e. first and second antigen); etc.

In some embodiments, the further binding site is directed against a serum protein so that the half-lie of the single domain antibody is increased. Typically, said serum protein is albumin.

Typically, the one or more further binding site may comprise one or more parts, fragments or domains of conventional chain antibodies (and in particular human antibodies) and/or of heavy chain antibodies. For example, a single domain antibody of the invention may be linked to a conventional (typically human) VH or VL optionally via a linker sequence.

In some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half life on the single domain antibody. In some embodiments, the at least one single domain antibody may also be linked to one or more (typically human) CH1, and/or CH2 and/or CH3 domains, optionally via a linker sequence. For instance, a single domain antibody linked to a suitable CH1 domain could for example be used—together with suitable light chains—to generate antibody fragments/structures analogous to conventional Fab fragments or F(ab')2 fragments, but in which one or (in case of an F(ab')2 fragment) one or both of the conventional VH domains have been replaced by a single domain antibody of the invention. In some embodiments, one or more single domain antibodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more typically from a conventional human chain antibody; and/or may form and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a single domain antibody), in which the Camelidae CH2 and/or CH3 domain have been replaced by human CH2 and CH3 domains, so as to provide an immunoglobulin that consists of 2 heavy chains each comprising a single domain antibody and human CH2 and CH3 domains (but no CHI domain), which immunoglobulin has the effector function provided by the CH2 and CH3 domains and which immunoglobulin can function without the presence of any light chains.

In some embodiment, the polypeptide is as described in WO2006064136. In particular the polypeptide may consist of i) a first fusion protein wherein the CL constant domain of an antibody is fused by its N-terminal end to the C-terminal end to a single domain antibody according to the invention (i.e. a single antibody directed against PN-1) and ii) a second fusion protein wherein the CH1 constant domain of an antibody is fused by its N-terminal end to the C-terminal end of a single domain antibody directed against an antigen different from PN-1. In another particular embodiment, the polypeptide consists of a first fusion protein wherein the CH1 constant domain of an antibody is fused by its N-terminal end to the C-terminal end of a single domain antibody directed against a an activating trigger molecule on an effector cell (e.g. CD16) and a second fusion protein wherein the CL constant domain of an antibody is fused by its N-terminal end to the C-terminal end to a single domain antibody of the invention (i.e. PN-1).

In some embodiments, the polypeptide of the present invention comprises at least one single domain antibodies comprising:

a CDR1 having the following sequence: $X_1$-T-W—$X_4$-$X_5$-E-I (SEQ ID NO: 20), wherein $X_1$ is S or D, $X_4$ is F or R, $X_5$ is R or L; and a CDR2 having the following sequence: S-X2-X3-X4-W-H-A (SEQ ID NO: 21), wherein X2 is D or E, X3 is P or D, X4 is T or G; and a CDR3 having a sequence set forth as SEQ ID NO:3 or SEQ ID NO:7.

In some embodiments, the polypeptide is a monoparatopic polypeptide. As used herein, the term "monoparatopic" polypeptide means a polypeptide comprising a single domain antibody of the invention that is linked to a second single domain antibody as herein defined, wherein these two single domain antibodies are directed against the same epitopes of one antigen.

In some embodiments, the monoparatopic antibody of the present invention comprises at least two single domain antibodies comprising a CDR1 having a sequence set forth as SEQ ID NO: 1, a CDR2 having a sequence set forth as SEQ ID NO:2 and a CDR3 having a sequence set forth as SEQ ID NO:3.

In some embodiments, the monoparatopic polypeptide of the present invention comprises at least two single domain antibodies having at least 70% of identity with sequence set forth as SEQ ID NO:4.

In some embodiments, the monoparatopic polypeptide of the present invention comprises at least two single domain antibodies having at least 70% of identity with sequence set forth as SEQ ID NO:4 and comprising CDR1, CDR2, CDR3 set forth as SEQ ID NO:1, SEQ ID NO:2 and SEQ ID NO:3.

In some embodiments, the monoparatopic polypeptide of the present invention comprises at least two single domain antibodies having a sequence set forth as SEQ ID NO:4.

In some embodiment, the monoparatopic polypeptide of the present invention comprises a sequence set forth as SEQ ID NO:17.

In some embodiments, the monoparatopic antibody of the present invention comprises at least two single domain antibodies comprising a CDR1 having a sequence set forth as SEQ ID NO: 5, a CDR2 having a sequence set forth as SEQ ID NO:6 and a CDR3 having a sequence set forth as SEQ ID NO:7.

In some embodiments, the monoparatopic polypeptide of the present invention comprises at least two single domain antibodies having at least 70% of identity with sequence set forth as SEQ ID NO:8.

In some embodiments, the monoparatopic polypeptide of the present invention comprises at least two single domain antibodies having at least 70% of identity with sequence set forth as SEQ ID NO:8 and comprising CDR1, CDR2, CDR3 set forth as SEQ ID NO:5, SEQ ID NO:6 and SEQ ID NO:7.

In some embodiments, the monoparatopic polypeptide of the present invention comprises at least two single domain antibodies having a sequence set forth as SEQ ID NO:8.

In some embodiments, the monoparatopic polypeptide of the present invention comprises at least two single domain antibodies comprising a CDR1 having the sequence set forth as SEQ ID NO:9; a CDR2 having the sequence set forth as SEQ ID NO:10; a CDR3 having a sequence set forth as SEQ ID NO:11.

In some embodiments, the monoparatopic polypeptide of the present invention comprises at least two single domain antibodies having at least 70% of identity with sequence set forth as SEQ ID NO:12.

In some embodiments, the monoparatopic polypeptide of the present invention comprises at least two single domain antibodies having at least 70% of identity with sequence set forth as SEQ ID NO:12 and comprising CDR1, CDR2, CDR3 set forth as SEQ ID NO:9, SEQ ID NO:10 and SEQ ID NO:11.

In some embodiments, the monoparatopic polypeptide of the present invention comprises at least two single domain antibodies having a sequence set forth as SEQ ID NO:12.

In some embodiments, the polypeptide is a biparatopic polypeptide. As used herein, the term "biparatopic" polypeptide means a polypeptide comprising a single domain antibody and a second single domain antibody as herein defined, wherein these two single domain antibodies are capable of binding to two different epitopes of one antigen (e.g. PN-1), which epitopes are not normally bound at the same time by one monospecific immunoglobulin, such as e.g. a conventional antibody or one single domain antibody. The biparatopic polypeptides according to the invention are composed of single domain antibodies which have different epitope specificities, and do not contain mutually complementary variable domain pairs which bind to the same epitope. They do therefore not compete with each other for binding to PN-1.

In some embodiments, the biparatopic polypeptide of the present invention comprises a B11 derivative as defined above and a F06 derivative as defined above.

In some embodiments, the biparatopic antibody of the present invention comprises i) a first single domain antibody comprising a CDR1 having a sequence set forth as SEQ ID NO: 1, a CDR2 having a sequence set forth as SEQ ID NO:2 and a CDR3 having a sequence set forth as SEQ ID NO:3 and ii) a second single domain antibody comprising a CDR1 having a sequence set forth as SEQ ID NO:5, a CDR2 having a sequence set forth as SEQ ID NO:6 and a CDR3 having a sequence set forth as SEQ ID NO:7.

In some embodiments, the biparatopic polypeptide of the present invention comprises i) a first single domain antibody having at least 70% of identity with sequence set forth as SEQ ID NO:4; and ii) a second single domain antibody having at least 70% of identity with sequence set forth as SEQ ID NO:8.

In some embodiments, the biparatopic polypeptide of the present invention comprises i) a first single domain antibody having at least 70% of identity with sequence set forth as SEQ ID NO:4 and comprising CDR1, CDR2, CDR3 set forth as SEQ ID NO:1, SEQ ID NO:2 and SEQ ID NO:3; and ii) a second single domain antibody having at least 70% of identity with sequence set forth as SEQ ID NO:8 and comprising CDR1, CDR2, CDR3 set forth as SEQ ID NO:5, SEQ ID NO:6 and SEQ ID NO:7.

In some embodiments, the biparatopic polypeptide of the present invention comprises i) a first single domain antibody having the sequence set forth as SEQ ID NO:4 and ii) a second single domain antibody having the sequence set forth as SEQ ID NO:8.

In some embodiment, the biparatopic polypeptide has a sequence set forth as SEQ ID NO:18.

In some embodiments, the biparatopic polypeptide of the present invention comprises a B11 derivative as defined above and a A08 derivative as defined above.

In some embodiments, the biparatopic antibody of the present invention comprises i) a first single domain antibody comprising a CDR1 having a sequence set forth as SEQ ID NO: 1, a CDR2 having a sequence set forth as SEQ ID NO:2 and a CDR3 having a sequence set forth as SEQ ID NO:3; and ii) a second single domain antibody comprising a CDR1 having a sequence set forth as SEQ ID NO:9, a CDR2 having a sequence set forth as SEQ ID NO:10 and a CDR3 having a sequence set forth as SEQ ID NO:11.

In some embodiments, the biparatopic polypeptide of the present invention comprises i) a first single domain antibody having at least 70% of identity with sequence set forth as SEQ ID NO:4; and ii) a second single domain antibody having at least 70% of identity with sequence set forth as SEQ ID NO:12.

In some embodiments, the biparatopic polypeptide of the present invention comprises i) a first single domain antibody having at least 70% of identity with sequence set forth as SEQ ID NO:4 and comprising CDR1, CDR2, CDR3 set forth as SEQ ID NO:1, SEQ ID NO:2 and SEQ ID NO:3; and ii) a second single domain antibody having at least 70% of identity with sequence set forth as SEQ ID NO:12 and comprising CDR1, CDR2, CDR3 set forth as SEQ ID NO:9, SEQ ID NO:10 and SEQ ID NO:11.

In some embodiments, the biparatopic polypeptide of the present invention comprises i) a first single domain antibody having the sequence set forth as SEQ ID NO:4 and ii) a second single domain antibody having the sequence set forth as SEQ ID NO:12.

In some embodiment, the biparatopic polypeptide has a sequence set forth as SEQ ID NO:19.

In some embodiments, the biparatopic polypeptide of the present invention comprises a F06 derivative as defined above and a A08 derivative as defined above.

In some embodiments, the biparatopic antibody of the present invention comprises i) a first single domain antibody comprising a CDR1 having a sequence set forth as SEQ ID NO: 5, a CDR2 having a sequence set forth as SEQ ID NO:6 and a CDR3 having a sequence set forth as SEQ ID NO:7; and ii) a second single domain antibody comprising a CDR1 having a sequence set forth as SEQ ID NO:9, a CDR2 having a sequence set forth as SEQ ID NO:10 and a CDR3 having a sequence set forth as SEQ ID NO:11.

In some embodiments, the biparatopic polypeptide of the present invention comprises i) a first single domain antibody having at least 70% of identity with sequence set forth as SEQ ID NO:8; and ii) a second single domain antibody having at least 70% of identity with sequence set forth as SEQ ID NO:12.

In some embodiments, the biparatopic polypeptide of the present invention comprises i) a first single domain antibody having at least 70% of identity with sequence set forth as SEQ ID NO:8 and comprising CDR1, CDR2, CDR3 set forth as SEQ ID NO:5, SEQ ID NO:6 and SEQ ID NO:7; and ii) a second single domain antibody having at least 70% of identity with sequence set forth as SEQ ID NO:12 and comprising CDR1, CDR2, CDR3 set forth as SEQ ID NO:9, SEQ ID NO:10 and SEQ ID NO:11.

In some embodiments, the biparatopic polypeptide of the present invention comprises i) a first single domain antibody having the sequence set forth as SEQ ID NO:8 and ii) a second single domain antibody having the sequence set forth as SEQ ID NO:12.

In some embodiments, the two single domain antibodies of the biparatopic or the monoparatopic polypeptide of the present invention can be linked to each other directly (i.e. without use of a linker) or via a linker. The linker is typically a linker peptide and will, according to the invention, be selected so as to allow binding of the two single domain antibodies to each of their at least two different epitopes of PN-1. Suitable linkers inter alia depend on the epitopes and, specifically, the distance between the epitopes on PN-1 to which the single domain antibodies bind, and will be clear to the skilled person based on the disclosure herein, optionally after some limited degree of routine experimentation. Also, when the two single domain antibodies that bind to PN-1 may also be linked to each other via a third single domain antibody (in which the two single domain antibodies may be linked directly to the third domain antibody or via suitable linkers). Such a third single domain antibody may for example be a single domain antibody that provides for an increased half-life. For example, the latter single domain antibody may be a single domain antibody that is capable of binding to a (human) serum protein such as (human) serum albumin or (human) transferrin, as further described herein. In some embodiments, two or more single domain antibodies that bind to PN-1 are linked in series (either directly or via a suitable linker) and the third (single) single domain antibody (which may provide for increased half-life, as described above) is connected directly or via a linker to one of these two or more aforementioned single domain antibodies. Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the anti-EGFR polypeptide of the invention is administered. One useful group of linker sequences are linkers derived from the hinge region of heavy chain antibodies as described in WO 96/34103 and WO 94/04678. Other examples are poly-alanine linker sequences such as Ala-Ala-Ala. Further preferred examples of linker sequences are Gly/Ser linkers of different length including (gly4ser)3 (SEQ ID NO: 22), (gly4ser)4 (SEQ ID NO: 23), (gly4ser) (SEQ ID NO: 24), (gly3ser) (SEQ ID NO: 25), gly3, and (gly3ser2)3 (SEQ ID NO: 26).

In some embodiments, it is contemplated that the polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

In some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half-life on the single domain antibody.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa). In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the polypeptide of the invention described herein for therapeutic delivery.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

Nucleic Acids, Vectors, Recombinant Host Cells and Uses Thereof

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art.

Accordingly, a further object of the invention relates to a nucleic acid molecule encoding a single domain antibody and/or a polypeptide according to the invention.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

So, a further aspect of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

Therapeutic Methods and Uses

The single domain antibodies and polypeptides of the invention are used as inhibitor of protease nexin-1 (PN-1).

Thus, the single domain antibodies and polypeptides of the invention are particularly suitable for the prevention or treatment of haemorrhagic diseases in subject in need thereof.

The present invention also relates to a method for preventing or treating haemorrhagic disease in a subject in need thereof, comprising administering to said subject an effective amount of the single domain antibodies and/or polypeptides of the present invention.

As used herein, the term "subject" denotes a mammal. In a preferred embodiment of the invention, a subject according to the invention refers to any subject (preferably human) afflicted with or susceptible to be afflicted with haemorrhagic diseases. In another preferred embodiment, a subject according to the invention refers to any subject (preferably human) afflicted with or susceptible to be afflicted with haemorrhagic diseases with deficiency in factor V, VIII, IX and/or XI.

As used herein, the term "haemorrhagic diseases" has its general meaning in the art and refers to haemorrhagic diseases such as revised in the World Health Organisation Classification D65-D69. The term "haemorrhagic diseases" also refers to constitutive haemorrhagic diseases, Rare bleeding disorders, haemorrhagic diseases with deficiency in factor V, VIII, IX and/or XI. The term "haemorrhagic diseases" also refers to haemorrhagic diseases such as haemophilia, Hereditary factor VIII deficiency (Haemophilia NOS, Haemophilia A, classical Haemophilia); Hereditary factor IX deficiency (Christmas disease, Deficiency in factor IX with functional defect, Deficiency in plasma thromboplastin component [PTC], Haemophilia B); coagulation defects such as Von Willebrand disease, Angiohaemophilia, Factor VIII deficiency with vascular defect, Vascular haemophilia; Hereditary factor XI deficiency (Haemophilia C, Plasma thromboplastin antecedent [PTA] deficiency); Hereditary deficiency of other clotting factors (Congenital afibrinogenaemia, Deficiency in AC globulin, proaccelerin, Deficiency of factor I [fibrinogen], II [prothrombin], V [labile], VII [stable], X [Stuart-Prower], XII [Hageman], and XIII [fibrin-stabilizing], Dysfibrinogenaemia (congenital), Hypoproconvertinaemia, Owren disease); Haemorrhagic disorder due to circulating anticoagulants (Haemorrhage during long-term use of anticoagulants, Hyperheparinaemia, Increase in antithrombin, anti-VIIIa, anti-IXa, anti-Xa, and anti-Xia, Coding-Hint); Acquired coagulation factor deficiency (Deficiency of coagulation factor due to liver disease and vitamin K deficiency); Primary Thrombophilia (Activated protein C resistance [factor V Leiden mutation], Deficiency in antithrombin, protein C and protein S, Prothrombin gene mutation); Other Thrombophilia (Anticardiolipin syndrome, Antiphospholipid syndrome, Presence of the lupus anticoagulant); Purpura, Allergic purpura, Qualitative platelet defects, Thrombocytopenia, Capillary fragility (hereditary) and Vascular pseudohaemophilia. The term "haemorrhagic diseases" also refers to bleeding episodes in haemorrhagic diseases like haemophilia and other rare bleeding disorders.

In some embodiment, the haemorrhagic disease is a haemorrhagic disease with deficiency in factor V, VIII, IX and/or XI.

In some embodiment, the haemorrhagic disease is haemophilia.

In some embodiment, the haemorrhagic disease is haemophilia A or haemophilia B.

In some embodiment, the haemorrhagic disease is mild or moderate haemophilia A

In some embodiment, the haemorrhagic disease is mild or moderate haemophilia B

The term "mild haemophilia A" has its general meaning in the art and refers to haemorrhagic disease defined by plasma FVIII of 5-40%.

The term "moderate haemophilia A" has its general meaning in the art and refers to haemorrhagic disease defined by plasma FVIII of 1-5%.

The term "severe haemophilia A" has its general meaning in the art and refers to haemorrhagic disease defined by plasma FVIII less than 1%.

The term "mild haemophilia B" has its general meaning in the art and refers to haemorrhagic disease defined by plasma FIX of 5-40%.

The term "moderate haemophilia B" has its general meaning in the art and refers to haemorrhagic disease defined by plasma FIX of 1-5%.

The term "severe haemophilia B" has its general meaning in the art and refers to haemorrhagic disease defined by plasma FIX less than 1%

Accordingly, the present invention also relates to the single domain antibodies and polypeptides of the present invention for use in the prevention of the development of coagulation factor resistance.

In some embodiment, the single domain antibody or the polypetide of the present invention is used in combination with classical treatment of haemorrhagic disease.

Thus, the invention refers to a method for preventing or treating haemorrhagic disease in a subject in need thereof, comprising administering to said subject i) an effective amount of the single domain antibodies and/or polypeptides of the present invention and ii) a classical treatment of haemorrhagic disease.

As used herein, the term "classical treatment of haemorrhagic disease" refers to any compound, natural or synthetic, used for the treatment of haemorrhagic disease.

According to the invention, compound used for the treatment of haemorrhagic disease may be selected in the group consisting of coagulation factor; desmopressin, antifibrinolytic medicine such as tranexamic acid and epsilon aminocaproic acid; fibrin sealants; antibody mimicking coagulation factor function such as Emicizumab.

As used herein, the term "antibody mimicking coagulation factor function" refers to antibody which exhibit the activity of coagulation factor, which is missing in haemophilia.

Antibody mimicking factor VIII function, such as Emicizumab, can bind to both activated coagulation factor IX and to factor X, mediating the activation of the latter.

In some embodiment, the single domain antibody or the polypetide of the present invention is used in combination with antibody mimicking factor VIII.

In some embodiment, the single domain antibody or the polypetide of the present invention is used in combination with Emicizumab.

Thus, in a further aspect, the present invention relates to the single domain antibodies and polypeptides according to the invention in combination with Emicizumab for use in the prevention or treatment of haemorrhagic disease in a subject in need thereof.

A used herein, the term "coagulation factor" has its general meaning in the art and refers to factor VIII (FVIII), factor IX (FIX), factor VIIa (FVIIa), plasma-derived activated prothrombin complex and fibrinogen. The term "coagulation factor" also relates to recombinant or purified coagulation factor.

In some embodiment, the single domain antibody or the polypetide of the present invention is used in combination with one or more coagulation factor.

Thus, in a further aspect, the present invention relates to the single domain antibodies and polypeptides according to the invention in combination with one or more coagulation factor for use in the prevention or treatment of haemorrhagic disease in a subject in need thereof.

Typically the single domain antibodies and polypeptides of the invention and the classical treatment of haemorrhagic disease as described above are administered to the subject in a therapeutically effective amount.

By a "therapeutically effective amount" of the single domain antibodies and polypeptides of the present invention as above described is meant a sufficient amount of the inhibitor. It will be understood, however, that the total daily usage of the inhibitors and compositions of the present invention will be decided by the attending physician within the scope of sound medical judgment. The specific therapeutically effective dose level for any particular subject will depend upon a variety of factors including the disorder being treated and the severity of the disorder; activity of the specific inhibitor employed; the specific composition employed, the age, body weight, general health, sex and diet of the subject; the time of administration, route of administration, and rate of excretion of the specific inhibitor employed; the duration of the treatment; drugs used in combination or coincidential with the specific inhibitor employed; and like factors well known in the medical arts. For example, it is well within the skill of the art to start doses of the the single domain antibodies and polypeptides of the invention at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the inhibitor of the present invention for the symptomatic adjustment of the dosage to the subject to be treated. A medicament typically contains from about 0.01 mg to about 500 mg of the single domain antibodies and polypeptides of the present invention, preferably from 1 mg to about 100 mg of the single domain antibodies and polypeptides of the present invention. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the single domain antibodies and polypeptides according to the invention may be used in a concentration between 0.01 μM and 20 μM, particularly, the inhibitor of the invention may be used in a concentration of 0.01, 0.05, 0.1, 0.5, 1.0, 2.5, 5.0, 10.0, 15.0, 20.0 μM.

The therapeutically effective amount of the coagulation factor of the invention is well known in the art. Typically, the therapeutically effective amount of the coagulation factor relates to coagulation factor (such as FVIII) between about 10 IU to 300 IU/kg body weight, especially from about 10 IU to 100 IU/kg body weight. Particularly, the therapeutically effective amount of the coagulation factor relates to coagulation factor amount of 10.0, 15.0, 20.0, 25.0, 30.0, 35.0, 40.0 IU/kg body weight.

In a particular embodiment, the coagulation factor according to the invention may be used in low doses to avoid the development of coagulation factor resistance. Typically, the term "low doses" refers to coagulation factor (such as FVIII) between about 5 IU to 40 IU/kg body weight. Particularly, the term "low doses" refers to coagulation factor amount of about 5.0, 10.0, 15.0, 20.0, 25.0, 30.0, 35.0, 40.0 IU/kg body weight.

According to the present invention, the single domain antibodies and polypeptides of the invention is administered sequentially or concomitantly with one or more coagulation factor.

Pharmaceutical Compositions and Kits of the Invention

Typically the single domain antibodies and polypeptides of the invention may be combined with pharmaceutically acceptable excipients, and optionally sustained-release matrices, such as biodegradable polymers, to form pharmaceutical compositions. Thus, the single domain antibodies and polypeptides of the invention is administered to the subject in the form of a pharmaceutical composition.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further agent which is used in the prevention or treatment of haemorrhagic disease.

In one embodiment, said additional active agents may be contained in the same composition or administrated separately.

In another embodiment, the pharmaceutical composition of the invention relates to combined preparation for simultaneous, separate or sequential use in the prevention and treatment of haemorrhagic disease.

Finally, the invention also provides kits comprising at least one single domain antibody or polypeptide of the invention. Kits containing an antin-PN-1 single domain antibody or polypeptide of the invention find use in therapeutic methods.

The invention will be further illustrated by the following figures and examples. However, these examples and figures should not be interpreted in any way as limiting the scope of the present invention.

FIGURES

FIG. 1: Identification and sequences of sdAbs isolated from a synthetic library. Non-adsorbed phage ELISA determining positive clones obtained after 3 rounds of phage display experiment. Phages were added to plates coated with hPN-1, mPN-1 or hPAI-1. An HRP-conjugated anti-M13 antibody and a colorimetric substrate were used to measure binding. VHH clones which showed a significant ELISA signal in the presence of mPN-1 and hPN-1 and a very low signal in the presence of hPAI-1 were considered specific.

FIG. 2: Characterization of VHHs obtained from a synthetic library. A-B. Wells were coated with mAb anti-PAI-1 and 2 μg/mL of hPAI-1 (A) or mPAI-1 (B) were incubated with VHHs (10 μg/mL). Bound VHHs were probed with peroxidase-labelled pAb anti-6×-His tag (SEQ ID NO: 27). C-D. Wells were coated with 0.5 g of hPN-1 (C) or mPN-1 (D) and incubated with different concentrations of monovalent VHHs (0.3 to 20 μg/mL). Bound VHHs were probed with peroxidase-labeled pAb-cMyc tag. E-F. One nM of thrombin was incubated with 10 nM hPN-1 (E) or mPN-1 (F) in the presence or absence of VHHs (10 μM). Residual thrombin activity was measured by the rate of PNAPEP-0238-hydrolysis substrate. Data (mean±SD; n=3-5) represent residual thrombin activity as percentage of thrombin alone. G. Urokinase plasminogen activator (u-PA; 1.3 nM) was incubated with hPAI-1 (10 nM) in the absence or presence of VHHs (10 μM). Residual uPa activity was measured by the rate of PNAPEP-1344-hydrolysis substrate. Data (n=3-5) represent residual u-PA activity as percentage of u-PA alone.

FIG. 3: Determination of half maximal inhibitory concentration of monovalent VHHs and strategy to identify and improve the best monovalent VHHs. A. hPN-1 or mPN-1 were incubated with different concentrations of monovalent VHHs (0-2 μM) and 1 nM of thrombin was added to each well. Residual thrombin catalytic activity was measured by assaying the rate of PNAPEP-0238-hydrolysis substrate. Data represent residual thrombin activity as percentage of thrombin alone. Each data point represents an individual measurement. The table recapitulates the IC50 obtained for the monovalent VHHs towards mPN-1 and hPN-1

(mean±SD; n=3). B. Strategy to select the best monovalent VHHs leading to the choice of bivalent VHHs in order to improve their properties.

FIG. 4: Characterization of bivalent VHHs: A-B. Wells were coated with 0.5 g of human (A) or murine PN-1 (B) and incubated with different concentrations of bivalent VHHs (0.3 to 20 µg/mL). Bound VHHs was probed with peroxidase-labeled pAb 6×His tag. C. hPN-1 or mPN-1 (10 nM) were incubated with different concentrations of bivalent VHHs (0-2000 nM) and 1 nM of thrombin was added to each well. Residual thrombin catalytic activity was measured by measuring the rate of PNAPEP-0238-hydrolysis. Residual thrombin catalytic activity was measured by assaying the rate of PNAPEP-0238-hydrolysis substrate. Data represent residual thrombin activity as percentage of thrombin alone. Each data point represents an individual measurement. The table recapitulates the IC50 obtained for the bivalent VHHs towards mPN-1 and hPN-1 (mean±SD; n=3). D. Representative BLI-analysis graphs (Octet) of VHH binding (100 µg/mL) to biotinylated peptides encompassing the RCL (50 µg/mL). Immobilized peptides were incubated in the absence (peptide-RCL) or presence of thrombin (peptide-RCL+IIa) (5 U/ml) for 30 min at 37° C. before exposure to VHHs. The Ctrl curve corresponds to the negative control. Results are expressed as the wavelength shift (in nm) generated by the binding of the different molecules.

FIG. 5: Ex vivo experiments of bivalent VHHs. A. Diluted murine wild-type plasma was incubated with 62.5 nM of mPN-1 and spiked with 288 nM of bivalent VHHs and prothrombin time (PT) was measured. B. Diluted FVIII-deficient murine plasma was incubated with 500 nM of mPN-1 and spiked with 625 nM of bivalent VHHs and a modified activated partial thromboplastin time (aPTT) was performed. C-D. 0.1 nM of thrombin was incubated with supernatant derived from non-activated (C) or TRAP-activated (D) platelets ($5 \times 10^8$ cells/mL) in the presence or absence of 1 µM bivalent VHHs. Residual thrombin catalytic activity was measured by the rate of PNAPEP 0238-hydrolysis substrate. Data (mean±SD; n=3-4) represent residual thrombin activity as percentage of thrombin alone.

EXAMPLE 1

Material & Methods

The inventors determined the inhibition of the anti-thrombin catalytic activity of human and murine PN-1 using the chromogenic substrate for thrombin S-2238 (Cryopep, Montpellier, France). S-2238 is a short peptide specific to thrombin covalently bound to pNA (4-nitroaniline). When cleaved by thrombin, it releases a free pNA which could be detected by a spectrophotometer at 405 nm. Human or murine PN-1 (20 nM) is incubated or not with bivalent hybribodies (B11-Bv, B11-F06 or B11-A08, at 10 or 1 µM) in a Hepes buffer (20 mM Hepes, 0.15 M NaCl, pH7.5-0.1% HSA) for 5 min at 37° C. before incubation with thrombin (1 nM) for 10 min at 37° C. followed by the addition of the chromogenic substrate S-2238 (2 mM). Changes in the absorbance were recorded at 405 nm for 90 min. Residual thrombin activity is expressed as the ratio of the activity measured in the presence of PN-1 incubated or not with the bivalent hybribodies to the activity of thrombin alone.

The inventors verified the specificity of the hybribodies for PN-1 by measuring the effect of the bivalent hybribodies on the inhibition of uPA by PAI-1, using the chromogenic substrate PNAPEP-1344 (Cryopep, Montpellier, France).

Human PAI (10 nM) is incubated or not with bivalent hybribodies (B11-Bv, B11-F06 or B11-A08, at 10 or 1 µM) in a PBS buffer containing 0.1% HSA) for 5 min at 37° C. before incubation with uPa (1.3 nM) for 10 min at 37° C. followed by the addition of the chromogenic substrate S-1344 (0.4 mM), starting the reaction. Changes in the absorbance were recorded at 405 nm for 120 min. Residual uPA activity is expressed as the ratio of the activity measured in the presence of PN-1 incubated or not with the bivalent hybribodies to the activity of uPA alone.

The inventors determined the IC50 of the bivalent hybribodies for human PN-1 using the chromogenic substrate for thrombin S-2238 (Cryopep, Montpellier, France). Human or murine PN-1 (20 nM) is incubated with increasing concentrations of bivalent hybribodies (B11-Bv, B11-F06 or B11-A08, at 10 or 1 µM) in Hepes buffer (20 mM Hepes, 0.15 M NaCl, pH7.5-0.1% HSA) for 5 min at 37° C. before incubation with thrombin (1 nM) for 10 min at 37° C., followed by the addition of the chromogenic substrate S-2238 (2 mM). Changes in the absorbance were recorded at 405 nm for 90 min. In the graph, % inhibition is equivalent to % of PN-1 activity.

Results

Inhibition of the Anti-Thrombin Activity of Human and Murine PN-1.

Using a llama-derived library, a total of 7 rounds of panning and 940 tested VHH, resulted in 52 candidates recognizing PN-1. Three nanobodies (B11, F06 and A08) were proven to be able to inhibit the anti-thrombin activity of human and murine PN-1. Dimeric combinations were tested and show better affinity and inhibitory activity. Indeed the hybribodies B11-Bv, B11-F06 and B11-A08 were able to inhibit the anti-thrombin activity of human and murine PN-1 (FIG. 2E-F).

First Specific Anti-PN-1 Antibodies.

Careful characterization of the candidates recognising PN-1 of the llama-derived library, revealed that all these VHH, resulted in 52 candidates recognizing also plasminogen activator inhibitor-1 (PAI-1). Moreover, all commercial anti-PN-1 antibodies that we tested also proved non-specific. Herein, the inventors found that the single domain antibodies B11, F06 and A08 and the hybribodies bivalents B11-Bv; B11-F06, B11-A08 bind efficiently to both human and murine PN-1 without cross-reactivity with PAI-1, the phylogenetically closest serpin relative of PN-1 (FIG. 2E-G).

The inventors previously showed that an inhibitor of PN-1, such as an anti-PN-1 antibody, improves thrombin generation in mild and moderate haemophilia patients. They establish that blocking PN-1 have a role in haemorrhagic disease treatment. Herein, the inventors described the first specific single domain antibodies able to block the anti-thrombin activity of both murine and human PN-1 without cross-reactivity with other serpins. These single domain antibodies can be a powerful tool in the treatment of haemorrhagic disease, in particular in haemophilia patients.

EXAMPLE 2

Materials & Methods

Materials

Isopropyl β-D-1-thiogalactopyranoside (IPTG), Human serum albumin (HSA), Bovine serum albumin (BSA) were from Sigma-Aldrich (Saint-Quentin Fallavier, France).

Polyclonal Rabbit anti-cMyc tag peroxidase-labelled, polyclonal rabbit anti-6×His-tag antibodies were from Abcam (Paris, France). Human and murine PN-1 and human α-thrombin were prepared as described.20,21 PT and aPTT reagents were from Stago-Diagnostica (Asnieres-sur-Seine, France). Chromogenic substrates PNAPEP-1344 and PNA-PEP-0238 were from Cryopep (Montpellier, France). Dynabeads M-450 epoxy beads, *E. coli* TG1 cells, Terrific Broth (TB)-medium, Lysogeny Broth (LB)-medium were from ThermoFisher Scientific (Villebon-sur-Yvette, France). Plasminogen activator inhibitor-1 (PAI-1) was from Stago BNL (Lille, France). AEBSF was from vWR (Fontenay-sous-Bois, France).

Construction of Anti-PN-1 VHHs from Lymphocytes Library by Phage Display

Immunization of a single llama (*L. glama*) was outsourced to the Centre de Recherche en Cancérologie (Université Aix-Marseille, Marseille, France).22 Briefly, the llama was immunized with 100 μg of a mix of human or murine PN-1 in equal proportion with Freund's incomplete adjuvant. After blood sampling, mRNA was extracted from lymphocytes and the VHH-library was constructed as described.22-24 The library contains VHH-coding DNA fragments, which were cloned into the pHEN6-phagemid vector and transformed in electrocompetent *E. coli* TG1 cells25 (ThermoFischer Scientific) to generate a library of 0.9×108 clones. The M13K07 phage helper was used to infect the TG1 VHH-library to allow surface expression of the VHHs.

Negative and Positive Selection of VHHs

To reduce the number of VHHs cross-reacting with PAI-1, phage particles were first incubated with beads coated with 100 g PAI-1 (1 h at room temperature in PBS-3% BSA). Non-binding phages were passed on beads coated with a mixture of murine PN-1 and human PN-1 (50 g of each). Captured phages were eluted with 0.5 mg/ml trypsin. Three consecutive rounds of enrichment were performed.

Selection of Anti-PN1-Specific VHHs.

After infection of TG1 bacteria with isolated phages, cells were grown 4 h under agitation in TB-medium, then 1 mM IPTG was added to induce VHH expression at 30° C. Eighteen hours after induction, cells were centrifuged and periplasmic extract was collected after lysis in TES-buffer (200 mM Tris-HCl, pH8, 0.5 mM EDTA and 500 mM sucrose) for 1 h at 4° C. followed by 30 min with TES-buffer diluted 4-fold in PBS. Released soluble proteins were tested for binding to PN-1, PAI-1 or BSA. Proteins (10 g/well) were coated on NUNC Maxisorp-plates (ThermoFischer Scientific) in PBS, overnight at 4° C. After saturation, (PBS-BSA 3%, 1 h at 37° C.), bound VHHs were probed using alkaline phosphatase-coupled polyclonal anti-6×His-tag antibody, detected via hydrolysis of 3,3',5,5'-tetramethylbenzidine (TMB) and absorbance was read at 450 nm.

Isolation of Anti-PN-1 VHH from a Synthetic Library.

In a second approach, a synthetic VHH library was used to isolate anti-PN-1 VHHs (Hybrigenics Services SAS, Paris, France). This hs2dAb phage-display library containing 3×109 VHHs was first incubated with human PAI-1-coated beads to reduce unspecific binders. Unbound VHHs were then incubated with murine or human PN-1-coated beads. A total of three rounds of phage display were performed, with the depletion step being repeated during each round. After 3 rounds, 90 *E. coli* clones were picked randomly and analyzed for binding to human and murine PN-1 as well as PAI-1. Phage-clones showing >5-fold increased signal to PN-1 over PAI-1 were considered as specific binders for PN-1 (mouse, human or both). Sequencing of the positive clones revealed the presence of 18 different positive VHHs. Four of these recognized both mPN-1 and hPN-1, and were subcloned in the pHEN2-vector for further characterization.

VHH Subcloning, Expression and Purification.

Anti-PN-1 VHHs were transformed directly into *E. coli* WK6 cells. Each clone was first grown in 10 mL LB-medium/100 μg/mL ampicillin/2% glucose/1 mM MgCl2 overnight at 37° C. under gentle agitation. 3 mL of this preculture was used to inoculate 330 mL of TB-medium/100 μg/mL ampicillin/0.1% glucose/1 mM MgCl2. The culture agitated (170 rpm, 37° C.) until it reached an OD600 between 0.8 and 1. VHH expression was then induced by 1 mM IPTG and the medium was left to grow overnight (170 rpm, 28° C.). The periplasmic proteins were extracted by sonication (Fisher scientific, Illkirch, France) during 30 min with a cycle 10 seconds ON/10 seconds OFF. The percentage of lysis was verified by a ratio (OD after lysis/OD before lysis)×100. His-tagged VHHs were next purified via Co2+-affinity chromatography as instructed (vWR). Minor contaminants were removed via size-exclusion chromatography using 20 mM Hepes (pH 7.4)/0.1M NaCl as equilibrium-buffer. Purified VHHs displayed >95% homogeneity as assessed via SDS-Page and Coomassie-staining. For bivalent VHHs, two copies of monovalent sdAbs were separated by a linker consisting of [GGGS]3 (SEQ ID NO: 28) and a C-terminal 6×His-Tag (SEQ ID NO: 27) allowed for purification via Co2+-affinity chromatography.

hPN-1 and mPN-1 ELISA.

Microlon-Med half-wells plates (Greiner bio-one, Courtaboeuf, France) were coated with 0.5 μg mPN-1 or hPN-1/well overnight at 4° C. and then incubated with different concentrations of VHHs (0 to 20 μg/mL) in PBS/BSA 0.1%/Tween-20 0.1% for 2 h at 37° C. Bound anti-PN-1 VHHs were probed with peroxidase-labelled polyclonal anti-cMyc tag antibody for monovalent VHHs or anti-6× His-tag antibody for bivalent VHHs in the same buffer and detected via hydrolysis of TMB and absorbance was read at 450 nm.

Inhibition of Thrombin Activity by PN-1

In a 96-wells plate (Greiner Bio-one) various concentrations of anti-PN-1 VHHs were incubated with 10 nM PN-1 during 15 min at room temperature in 20 mM Hepes/0.15M NaCl/0.1% HSA. 1 nM purified thrombin was then added to the wells and incubated 30 min at room temperature. Thrombin activity was quantified by measuring the rate of p-nitroaniline release from the chromogenic substrate H-D-Phe-Pip-Arg-pNA (PNAPEP-0238) (0.2 mM), at 37° C. and read at 405 nm in a multiwell plate reader. To calculate the IC50 of each VHH, a slightly modified protocol was used: anti-PN-1 VHHs were used at concentrations between 0 and 2 μM, incubation of VHHs was performed during 5 min followed by 10 min incubation with 1 nM thrombin. PNA-PEP-0238 substrate was added at a concentration of 0.2 mM and incubated for 2 h at 37° C. Quantification of thrombin activity was performed as described above.

Inhibition Thrombin Activity by Endogenous PN-1

Blood samples were taken in ACD-A anticoagulant tubes. Blood was centrifuged at 120 g during 15 min to recover the platelet rich plasma (PRP). Then, 2 μL/mL apyrase (5 mg/mL) and 1 μL/mL PGE1 (10 mM) were added and the PRP was centrifuged at 1200 g, 12 min at 20° C. The pellet was resuspended gently in washing buffer (3.6 mM citric acid, 0.5 mM glucose, 0.5 mM KCl, 10.3 mM NaCl, 2 mM CaCl2) pH6.5, 0.30% BSA, 2 μL/mL apyrase (5 mg/mL) and 1 μL/mL PGE1 (10 mM)) and centrifuged 12 min at 1200 g at 20° C. The platelets were adjusted to a concentration of 5×108 cells/mL in reaction buffer (0.03 mM NaH2PO4, 0.5 mM Hepes, 0.55 mM glucose, 0.2 mM MgCl2, 0.1 mM KCl, 13.7 mM NaCl, 12 mM NaHCO$_3$, 2 mM CaCl2), pH 7.3 and 0.3% BSA). For the condition "activated platelets", 50 μM of TRAP (Thrombin receptor activating peptide) was added to the platelets for 30 min at 37° C. Platelet were centrifuged 1200 g for 10 min at room temperature to keep the supernatant. In a 96-wells plate (Greiner Bio-one), 80 μL of activated or non-activated platelets supernatant was spiked with 1 μM of VHHs and incubated 15 min at room temperature. Then, 0.1 nM of thrombin was added to each well and incubated 30 min at room temperature. PNAPEP-0238 substrate was added at a concentration of 0.2 mM and incubated for 2 h at 37° C. Quantification of thrombin activity was performed as described above.

Inhibition of uPA (Urokinase-Type Plasminogen Activator) by Human PAI-1

In a 96-wells plate (Greiner Bio-one), 10 μM anti-PN-1 VHHs were incubated with 10 nM PAI-1 for 15 min at room temperature in 20 mM Hepes pH7.5, 150 mM NaCl, 0.1% HSA, pH7.5. 1.3 nM of uPA was subsequently added. After 10 min incubation at room temperature, wells were quantified for uPA activity by measuring the rate of p-nitroaniline release from the chromogenic substrate Glu-Gly-Arg-pNA, PNAPEP-1344 (0.2 mM) at 37° C. and read at 405 nm by a multiwell plate reader.

Test of VHHs Specificity by Biolayer Interferometry (BLI)-Analysis

Equilibrium binding was performed via BLI-analysis using Octet QK-equipment (Fortebio, Reading, UK). Monovalent VHHs (25 μg/mL) diluted in 100 mM MES (pH 5.0) were immobilized onto amine reactive biosensors. After quenching by ethanolamine, VHHs-coated sensors were incubated with human or murine PN-1 or human PAI-1 (1 μM) in PBS-Tween 0.1% buffer for 15 min to allow association. Subsequently, biosensors were incubated in PBS-Tween 0.1% buffer for 10 min to initiate dissociation. In alternative experiments, 50 μg/mL biotinylated RCL of PN-1 was immobilized on streptavidine sensors in PBS-Tween 0.1% buffer. Before the association, 5 U of thrombin or buffer PBS-Tween were incubated with sensor during 30 min at 37° C. then the association of bivalent VHHs (100 μg/mL) was followed for 15 min at 37° C. Subsequently, biosensors were put in PBS-tween 0.1% buffer for 10 min to initiate dissociation. Data were analyzed using Octet Software version 4.0.

Modified Prothrombin Time (PT)

Fifty microliters of murine normal pooled plasma (MNPP) were diluted 8-fold in Owren-Koller buffer and 50 μL FII-deficient (Prothrombin-deficient) lyophilised plasma (Stago-Diagnostica) were added. The mix was incubated 15 min at 37° C. with 62.5 nM of mPN-1 with or without 288 nM bivalent VHHs. Prothrombin time was started by adding 100 μL Neoplastin CI (Stago-Diagnostica) to the mix. Clot formation was measured by coagulometer STArt, (Stago-Diagnostica). Assays were performed three times in duplicates at 37° C.

Modified Activated Partial Thromboplastin Time (aPTT)

Fifty microliters of FVIII-deficient murine plasma were diluted 8-fold in Owren-Koller buffer to which 50 μL of FVIII-deficient lyophilised plasma and 50 μL of PTT reagent (Stago-Diagnostica) were added. After a 100 seconds incubation, 625 nM VHHs and 500 nM mPN-1 were added. After 240 seconds of incubation at 37° C., the aPTT test was started by adding 100 μL 0.025M CaCl2). The clot formation was measured by a coagulometer. Assays were performed three times in duplicates at 37° C.

Statistical Analysis

Data are presented as mean with standard error (SD) and was analyzed using Prism software. One-way ANOVA analysis was utilized for values comparisons with control. P-values <0.05 & P<0.0001 were considered as significant and highly significant respectively.

Results

Developing Anti-PN-1 VHHs from a Synthetic VHHs Library.

To obtain specific potent inhibitory anti-PN-1 VHHs, we used a synthetic VHH library. The VHH were selected using the same protocol used for classical VHHs. The 4 strongest binders were selected for further characterization: H12, B11, F06 and A08. The hPN-1, mPN-1 and PAI-1 non-adsorbed phage ELISA presented in FIG. 1 highlights the distinct recognition of all 4 VHHs for hPN-1 and mPN-1 as well as their non-recognition of hPAI-1.

Characterization of Anti-PN-1 VHHs Obtained from the Synthetic Library

The purified VHHs were analysed for their interaction with PAI-1 and both hPN-1 and mPN-1. In line with the initial screening, none of the 4 selected VHH displayed relevant binding to human or murine PAI-1 (FIG. 2A-B). In contrast, VHHs H12, B11, F06 and A08 all displayed dose-dependent binding to both human and murine PN-1 (FIG. 2C-D). To assess the inhibitory activity of the different VHHs towards PN-1, we next performed an assay measuring thrombin activity in the presence of PN-1 and the various VHHs. Although being most efficient in binding to both hPN-1 and mPN-1, VHH H12 interfered only partially with PN-1-mediated inhibition of thrombin activity, restoring thrombin activity to 74±5% and 53±17% for hPN-1 and mPN-1, respectively (FIG. 2E-F). VHHs B11, F06 and A08 proved more efficient in lifting hPN-1 inhibition of thrombin, with a recovery of thrombin activity of 100±7% for B11, 100±5% for F06 and 100±11% for A08, (FIG. 2E). A similar potent inhibitory capacity was also observed for mPN-1: 92±10% for B11, 96±9% for F06 and 94±14% for A08 (FIG. 2F). None of these VHHs affected inhibition of u-PA by PAI-1 (FIG. 2G). In conclusion, this second selection strategy did generate VHHs being selective and inhibitory towards both hPN-1 and mPN-1.

Determination of the IC50 for B11, F06, A08 VHHs

Figure 3A:
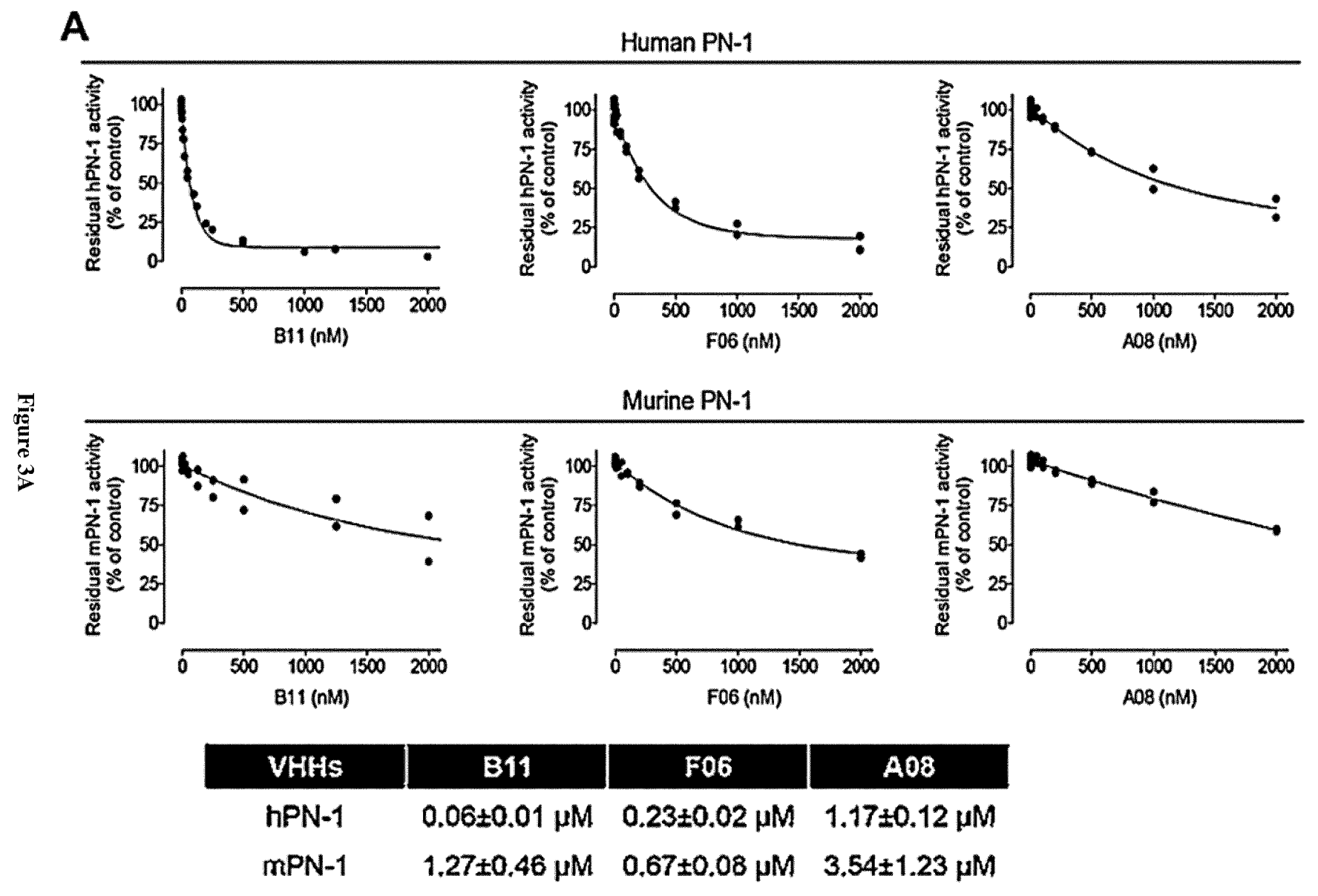

In order to determine the half maximum inhibitory concentration of B11, F06 and A08 towards hPN-1 and mPN-1, we incubated various concentrations of VHHs with 10 nM PN-1 and 1 nM thrombin. The degradation of PNAPEP-0238 substrate was followed for 2 hours. The calculated IC50 values for the tested VHHs towards hPN-1 were 0.05±0.01 μM for B11, 0.29±0.03 μM for F06, and 0.96±0.39 μM for A08 (FIG. 3A). Using mPN-1, the respective calculated values of IC50 were 1.58±0.24 μM for B11, 0.56±0.13 μM for F06, and 2.88±0.77 μM for A08 and (FIG. 3A). To increase the inhibitory effect of the VHHs especially towards mPN-1, we next generated 3 different bivalent constructs, B11bv, B11F06 and B11A08 (FIG. 3B). Following this engineering step, we verified whether the purified bivalent VHHs had kept their ability to bind hPN-1 and mPN-1 (FIG. 4A-B). We also confirmed that they still did not recognize PAI-1 (not shown).

Figure 4C:
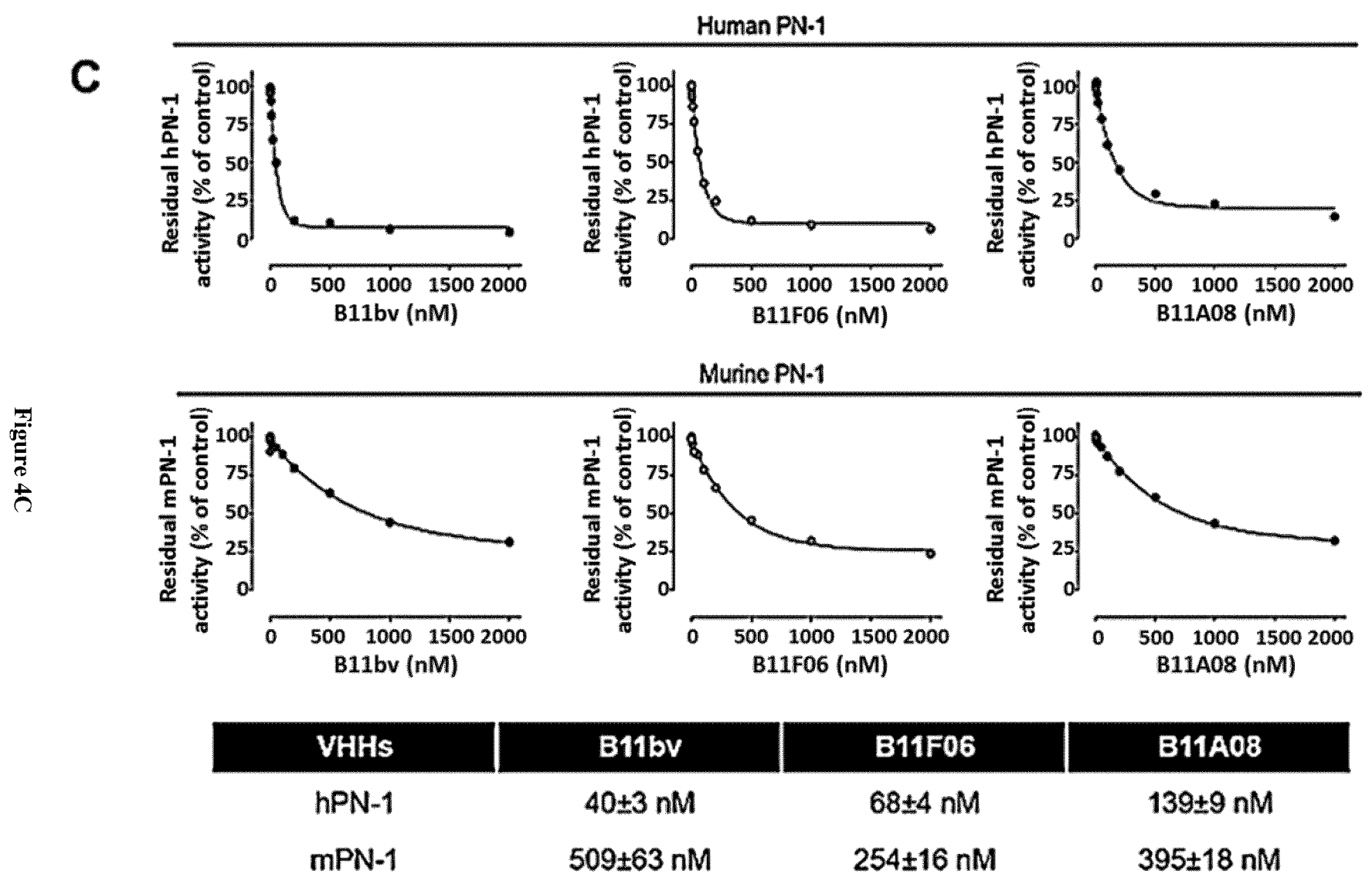

The IC50 of the bivalent VHHs were markedly improved compared to monovalent VHHs with values of 41±7 nM for B11bv, 62±6 nM for B11F06 and 142±28 nM for B11A08 towards hPN-1. For mPN-1, the IC50 were also improved with values of 825±9 nM, 414±141 nM and 524±174 nM for B11bv, B11F06 and B11A08 respectively (FIG. 4C).

Figure 4D:
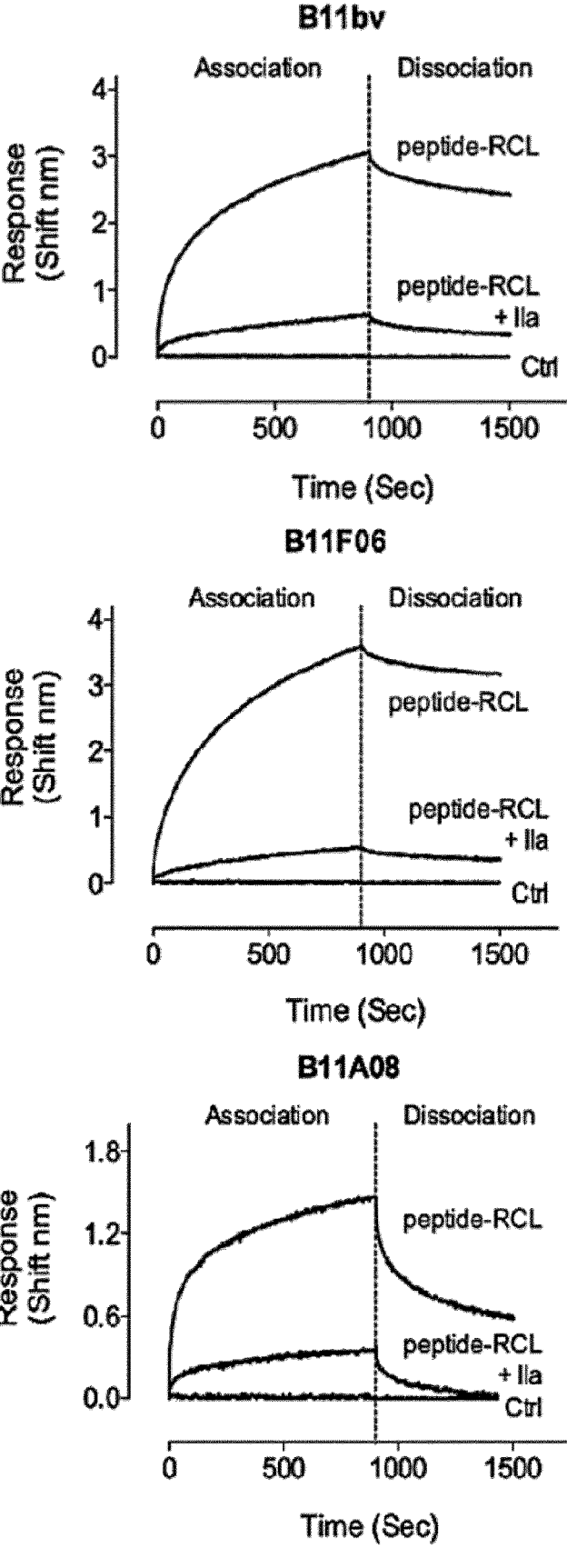

In an attempt to identify the binding region of the VHHs on PN-1, we performed BLI-analysis to test the interaction between a peptide covering the RCL region of PN-1 (either intact or after cleavage by thrombin) and the bivalent VHHs. All three bivalent sdAbs bound efficiently to the RCL peptide, demonstrating that they are directed against this area of the protein (FIG. 4D). Binding to this peptide was strongly reduced for each bivalent construct upon RCL cleavage by thrombin. These data are compatible with VHH B11 binding to the C-terminal portion of the RCL (which is released from the sensor after thrombin cleavage) or to an epitope overlapping the P1-P'1 cleavage site. None of the VHHs appear to recognize the N-terminal portion of the RCL (which remains bound to the sensor after thrombin cleavage). The data do not distinguish between F06 and A08 binding to the C-terminal portion of the RCL or to an epitope outside the RCL.

Effect of Bivalent VHHs on In Vitro Coagulation Assays.

To test the effect of bivalent VHHs on coagulation, we performed modified PT and aPTT coagulation assays with mPN-1 using murine plasma.

Figure 5A:
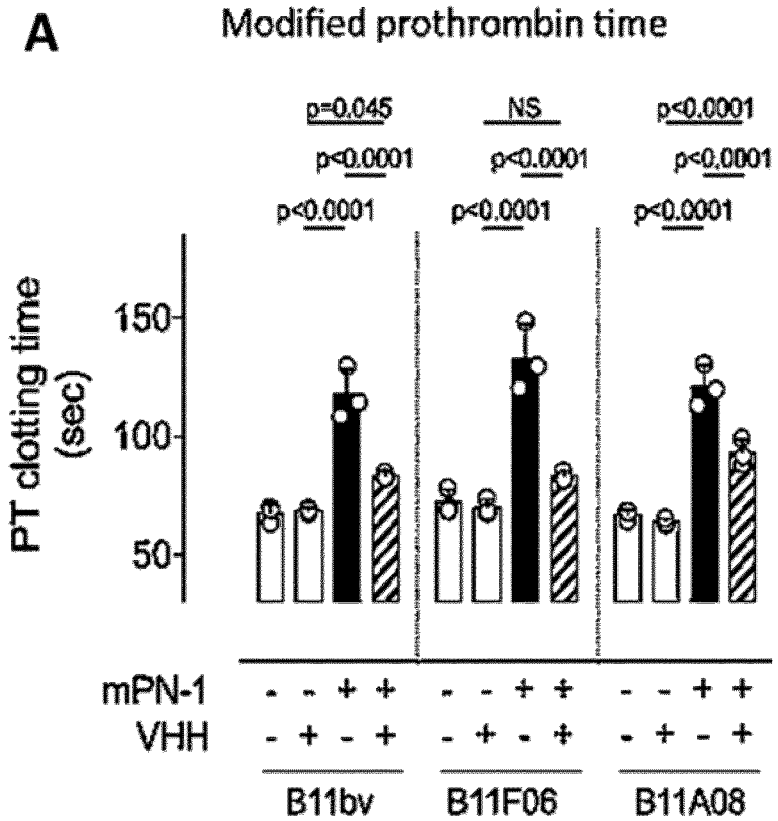

First, a PT was developed using wild-type plasma incubated with a prothrombin deficient lyophilised plasma in order to be able to use only small quantities of mPN-1. Using this modified assay, PT was 69.0±2.4 sec and increased to 123.8±6.6 sec after addition of 62.5 nM mPN-1 (FIG. 5A). At a concentration of 288 nM, all three bivalent VHHs were able to restore the PT, while not affecting PT in the absence of added mPN-1 (83.5±1.1 sec for B11bv; 83.3±1.5 sec for B11F06; 93.2±4.4 sec for B11A08). In this assay, B11A08 was slightly less efficient that the other two VHHs.

Figure 5B:
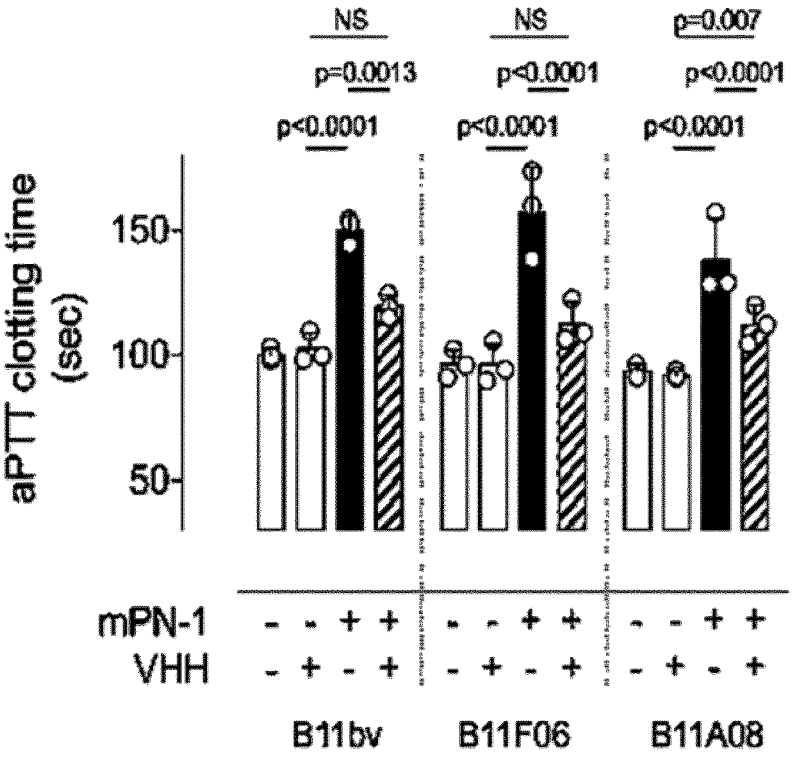

We also tested the effect of bivalent VHHs in a modified aPTT (FIG. 5B). Similar to the PT, we designed specific conditions where aPTT is increased, by using F8-deficient murine plasma in order to make the test more sensitive to PN-1. aPTT in F8-deficient murine plasma was 97.0±2.7 sec and increased 1.6-fold to 148.4±7.9 sec when mPN-1 was added. The three VHHs decreased significantly the aPTT, with B11F06 being most efficient (112.5±7.0 sec; FIG. 5B).

Figure 5C:
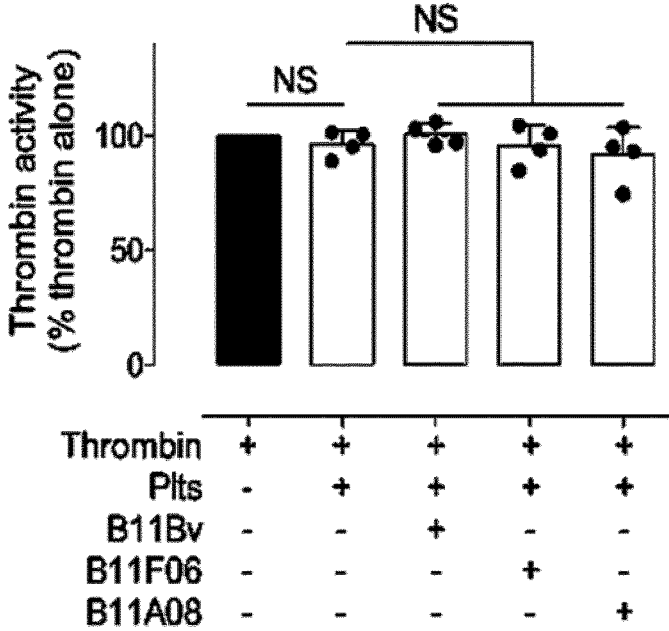
Figure 5D:
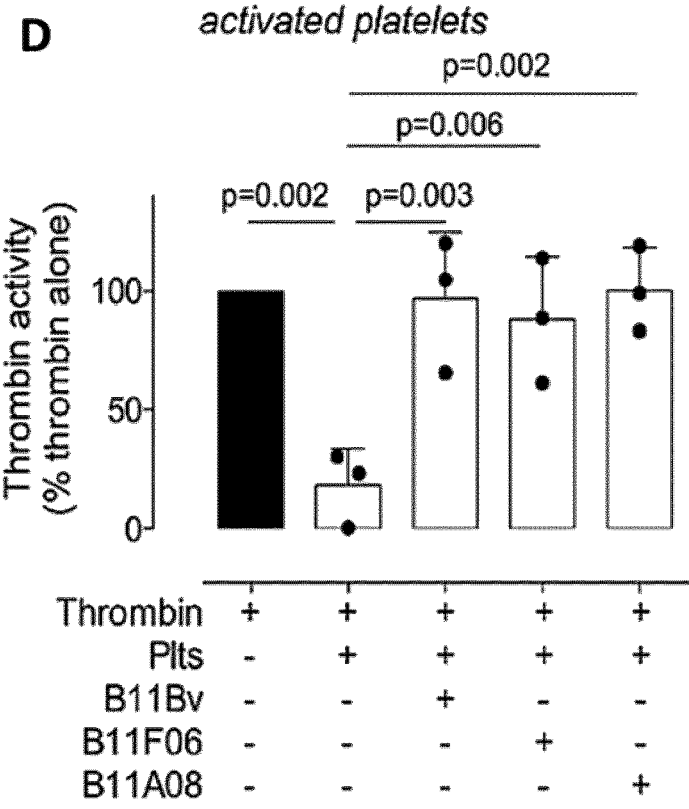

We next investigated whether our bivalent VHHs were also able to inhibit endogenous PN-1 present in platelet alpha granules. For this experiment, supernatant from non-activated or TRAP-activated platelets was used as a source of PN-1. The efficacy of secreted PN-1 in inhibiting thrombin activity was thus investigated. As expected, when supernatant from non-activated platelets was incubated with thrombin, no inhibitory effect was measured since PN-1 had not been released from platelet α-granules (FIG. 5C). In contrast, residual thrombin activity dropped to 18±15% in the presence of supernatant derived from TRAP-activated platelets (FIG. 5D). The bivalent VHHs abolished the inhibition of thrombin activity by the secreted platelet PN-1, thrombin activity being restored to 97±23% for B11bv, 88±21% for B11F06 and 100±15% for B11A08.

We have previously shown, that platelets release PN-1 following their activation, and that this PN-1 impairs the generation of thrombin. Indeed, by using supernatants of non-activated and TRAP-activated platelets, we could confirm the release of a thrombin-inhibitory molecule (FIG. 5C-D). Interestingly, this inhibitory effect could be neutralized by the addition of VHHs, demonstrating that they are able to interact with and inhibit PN-1 that is released from platelets.

Altogether, we have developed a strategy for the development of inhibitory VHHs targeting PN-1, which do not cross-react with PAT-1. These VHHs can be used as research tools to better understand the role of PN-1 in physiological and pathological processes. In addition, they may be explored for their potential therapeutic application in haemophilia treatment for instance.

REFERENCES

Throughout this application, various references describe the state of the art to which this invention pertains. The disclosures of these references are hereby incorporated by reference into the present disclosure.

Boulaftali Y, Adam F, Venisse L, Ollivier V, Richard B, Taieb S, Monard D, Favier R, Alessi M C, Bryckaert M, Arocas V, Jandrot-Perrus M, Bouton M C. Anticoagulant and antithrombotic properties of platelet protease nexin-1. Blood. 2010; 115: 97-106.

Bouton M C, Boulaftali Y, Richard B, Arocas V, Michel J B, Jandrot-Perrus M. Emerging role of serpinE2/protease nexin-1 in hemostasis and vascular biology. Blood. 2012 Mar. 15; 119(11):2452-7.

McGrogan M, Kennedy J, Li M P, et al. Molecular cloning and expression of two forms of human protease nexin T. Biotechnology. 1988; 6:172-177.

The invention claimed is:

1. A single domain antibody (sdAb) that targets protease Nexin-1 comprising formula (I), wherein the amino acid sequence of formula (I) has three complementary determining regions (CDR1, CDR2, and CDR3) and four framework regions (FR1 to FR4) from N-terminus to C-terminus:

FR1-CDR1-FR2-CDR2-FR3-CDR3-FR4    (I); wherein

CDR1 has the amino acid sequence set forth as SEQ ID NO: 1, CDR2 has the amino acid sequence set forth as SEQ ID NO:2 and CDR3 has the amino acid sequence set forth as SEQ ID NO:3.

2. The single domain antibody according to claim 1 having at least 95% identity with the amino acid sequence set forth as SEQ ID NO:4.

3. The single domain antibody according to claim 1 which comprises the amino acid sequence set forth as SEQ ID NO:4.

4. A pharmaceutical composition comprising the single domain antibody of claim 1 and/or a polypeptide comprising
   at least one copy of the single domain antibody and
   a pharmaceutically acceptable carrier.

5. A polypeptide comprising the single domain antibody according to claim 1.

6. The polypeptide according to claim 5 further comprising a second single domain antibody comprising an amino acid sequence of formula (I) comprising three complementary determining regions (CDR1a, CDR2b and CDR3c) and four framework regions (FR1 to FR4):

FR1-CDR1a-FR2-CDR2b-FR3-CDR3c-FR4    (I); wherein:

CDR1a has the amino acid sequence set forth as SEQ ID NO: 5 CDR2b has the amino acid sequence set forth as SEQ ID NO:6 and CDR3c has the amino acid sequence set forth as SEQ ID NO:7.

7. The polypeptide according to claim 5 further comprising:
   a second single domain antibody comprising an amino acid sequence of formula (I) comprising three complementary determining regions (CDR1d, CDR2e, and CDR3f) and four framework regions (FR1 to FR4):

FR1-CDR1d-FR2-CDR2e-FR3-CDR3f-FR4    (I); wherein

CDR1d has the amino acid sequence set forth as SEQ ID NO:9;
CDR2e has the amino acid sequence set forth as SEQ ID NO:10; and
CDR3f has the amino acid sequence set forth as SEQ ID NO:11.

8. The polypeptide according to claim 5 which comprises the amino acid sequence set forth as SEQ ID NO:17.

9. The polypeptide according to claim 6 which comprises the amino acid sequence set forth as SEQ ID NO:18.

10. The polypeptide according to claim 7 which comprises the amino acid sequence set forth as SEQ ID NO:19.

11. A pharmaceutical composition comprising the polypeptide according to claim 6 and a pharmaceutically acceptable carrier.

12. A pharmaceutical composition comprising the polypeptide according to claim 7 and a pharmaceutically acceptable carrier.

* * * * *